(12) United States Patent
Ehlbeck et al.

(10) Patent No.: US 8,557,187 B2
(45) Date of Patent: Oct. 15, 2013

(54) METHOD AND DEVICE FOR PLASMA-SUPPORTED SURFACE TREATMENT

(75) Inventors: Joerg Ehlbeck, Hinrichshagen (DE); Ruediger Foest, Neuenkirchen (DE); Eckhard Kindel, Greifswald (DE); Norbert Lembke, Greifswald (DE); Manfred Stieber, Greifswald (DE); Klaus-Dieter Weltmann, Binz (DE)

(73) Assignee: Neoplas GmbH, Greifswald (DE)

( * ) Notice: Subject to any disclaimer, the term of this patent is extended or adjusted under 35 U.S.C. 154(b) by 182 days.

(21) Appl. No.: 12/705,089

(22) Filed: Feb. 12, 2010

(65) Prior Publication Data

US 2010/0292757 A1 Nov. 18, 2010

Related U.S. Application Data

(63) Continuation of application No. PCT/EP2008/059840, filed on Jul. 26, 2008.

(30) Foreign Application Priority Data

Aug. 8, 2007 (DE) .......................... 10 2007 037 406

(51) Int. Cl.
*A61L 2/00* (2006.01)
*B01J 19/00* (2006.01)

(52) U.S. Cl.
USPC ............................................ 422/130; 422/22

(58) Field of Classification Search
USPC ................................................ 422/22, 130
See application file for complete search history.

(56) References Cited

U.S. PATENT DOCUMENTS

| | | | |
|---|---|---|---|
| 2002/0187066 A1* | 12/2002 | Yu et al. ........................ | 422/22 |
| 2005/0162647 A1* | 7/2005 | Okumura et al. ............. | 356/316 |
| 2006/0040067 A1 | 2/2006 | Culp et al. | |
| 2007/0159517 A1 | 7/2007 | Hashimoto et al. | |

FOREIGN PATENT DOCUMENTS

| | | |
|---|---|---|
| DE | 20 2004 016 083 U1 | 3/2006 |
| EP | 0 355 622 A2 | 2/1990 |
| WO | WO 93/05890 | 4/1993 |

* cited by examiner

*Primary Examiner* — Walter D Griffin
*Assistant Examiner* — Christopher Vandeusen
(74) *Attorney, Agent, or Firm* — Oblon, Spivak, McClelland, Maier & Neustadt, L.L.P.

(57) ABSTRACT

A method and a series of devices for dry cleaning, activating, modifying, coating, and biologically decontaminating (de-germing, disinfecting, sterilizing) surfaces by means of an atmospheric pressure plasma generated using a surface barrier discharge are provided. The invention is used for dry cleaning, activating, coating, modifying, and biologically contaminating surfaces by means of an atmospheric pressure plasma generated in a defined, flowing gas atmosphere by a surface barrier discharge, comprising a high-voltage electrode that is covered with a dielectric or ferroelectric material, an electrically conducting grounded contact electrode, a high-voltage supply, a gas supply, and a gas nozzle (encompassing a gas outlet); said gas nozzle is located in the direct vicinity of the grounded contact electrode, is integrated into the contact electrode, or acts as the grounded contact electrode.

22 Claims, 25 Drawing Sheets

METHOD AND DEVICE FOR PLASMA-SUPPORTED SURFACE TREATMENT

BACKGROUND OF THE INVENTION

1. Field of the Invention

The invention relates to a method and to a series of devices for dry cleaning, activation, coating, modification, and biological decontamination (such as degerming, disinfection, sterilization) of surfaces by means of an atmospheric pressure plasma produced by means of so-called surface barrier discharge.

2. Description of the Related Art

Plasma technology methods can already be used, in standard manner, for treating material surfaces with the goal of cleaning (i.e. decontaminating), activating, functionalizing or coating the surface, in order to prepare it for subsequent technological processes, such as gluing, printing, varnishing, or to be able to carry work out under germ-free conditions. In the past, low-pressure plasmas were primarily used for this, particularly for complex surface geometries. Due to the high system costs for the vacuum apparatuses required for this, the discontinuous method of operation, as well as because the dimensions of the work pieces to be treated are restricted by the size of the recipient used, use of low-pressure plasma methods for large-scale technical applications is only possible with restrictions, particularly in industrial line production. Atmospheric pressure plasmas are used for integrating plasma technology methods of surface treatment into industrial production lines. Plasmas of this type can be produced, for example, by means of corona discharge or barrier discharge. However, they can also be used in the form of normal pressure jet plasmas that are generated on the basis of corona discharge, barrier discharge, or arc discharge, by means of implementing suitable process gas streams.

Methods and devices for surface treatment that are based on the use of such plasmas are described in numerous journals and, in part, also already used for different applications. However, the technical solutions described in these documents are connected with at least one or more of the following disadvantages:

Complicated, expensive power supply devices are needed.

Relatively high operating costs result from high energy consumption and, in part, also from a high gas consumption and from required cooling.

Uniform treatment (particularly coating) of the material is made difficult by the non-homogeneous structure of the plasmas.

In many cases, the discharges are non-homogeneous and consist of many small, energy-rich micro-discharges, which can lead to local material damage.

The devices cannot be used universally for simply any work pieces. Either they are suitable only for treatment of planar materials having a material thickness restricted to a few millimeters (such as foils and web materials, for example), or they can only be adapted to work pieces having a complex geometry by means of complicated positioning systems.

The devices cannot be used as manual devices for manually guided operation.

The documents listed below also belong to the state of the art. In DE 195 32 412 A1, a method for surface pre-treatment of work pieces by means of a plasma jet is described, whereby the plasma jet is at first generated in a nozzle with electrodes, as an arc, and transferred onto the work piece to be treated, out of the electrode array, by means of a swirled working gas stream. In DE 298 05 999 U1, a device is described that carries a plasma jet directed parallel to the axis of rotation, by means of a rotation head having at least one eccentrically disposed plasma nozzle, as described above, and can plasma-treat surfaces. DE 10 2004 033 728 A1 describes a method for processing and gluing work pieces made of metal or a metal alloy having a hydrated oxide and/or hydroxide layer, whereby cleaning, activation, and subsequent treatment take place using an atmospheric plasma jet. DE 199 27 557 A1 describes a method for pre-treatment of work pieces to be welded or soldered, whereby a high-frequency arc discharge is provided between an electrode and the surface of the work piece to be treated. The device and method described here demonstrate significant differences from the methods and devices according to the invention described later. The electrode array is always structured in such a manner that the electrodes are situated on or in the immediate vicinity of the work pieces, and the plasma is produced directly at its location of effect, if possible. The gas stream used does not have the function of carrying the plasma out of the electrode array to the work piece, or to cool the electrode array, as in the case of the plasma jets, but rather merely serves for local intensification of the plasma at its location of effect and for control of its parameters (including the type and condition of the excited species). Because of the special electrode array, the gas consumption is kept very low, and the ignition voltage required for plasma operation is minimized. Thus, the required power supply devices can be structured to be very small, simple, and compact.

In DE 43 25 939 C1, WO 2004/053185 A1, and DE 38 27 629 A1, methods and devices for surface treatment are described, which are based on so-called volume barrier discharge (also called silent discharge, dielectrically inhibited discharge, or corona treatment). Experience has shown that the usability of so-called corona discharge systems is practicable only for the treatment of planar materials having a material thickness of a few millimeters (for example foils and web materials). In WO 2004/053185 A1, an electrode covered by a dielectric is used, in order to produce plasma in a reactive gas stream, in order to preserve metal surfaces, which function as a counter-electrode at the same time, by means of the plasma treatment. DE 38 27 629 A1 presents a method for surface pre-treatment of electrically conductive shaped materials, such as metal foil webs or plastic films into the polymatrix of which electrically conductive particles are embedded. The discharge is produced between discharge electrodes mantled by dielectric material and the metal core of a roller that serves as a grounded counter-electrode, whereby the foil web to be treated is transported over the roller. In addition, the working gas can be provided with an aerosol capable of being suspended in air, by means of an atomization device. In both cases, the counter-electrode and the discharge electrodes mantled by dielectric material form a discharge gap, so that so-called cold plasma is produced in the volume. In two of the aforementioned patents (DE 43 25 939 C1, WO 2004/053185 A1), so-called indirect corona treatments are also described. The corona nozzle presented in DE 43 25 939 C1 serves for indirect plasma treatment of web-form or profiled materials, and has at least two high-voltage electrodes between which an air stream that is guided to oscillate or circulate exits. In WO 2004/053185 A1, a so-called indirect barrier discharge is described for preserving metal surfaces. In both cases, the gas stream has the task, similar to a plasma jet, of driving the discharge out of the space between the two electrodes and onto the work piece to be treated. The gas stream thus acts on the shape and surface structure of the plasma. Three versions of the rotating or circulating guidance of the air stream are described.

In DE 102 19 197 C1, a method and a device for treating the surface of a metal wire, particularly as a coating pre-treatment, are described. In this connection, an alternating high voltage is applied to a metal wire on an electrode that is provided with a dielectric shield in the direction of the metal wire, in order to bring about a volume barrier discharge in the gas chamber, over the surface of the metal wire.

SUMMARY OF THE INVENTION

It is an object of the invention to provide a method for plasma-supported surface treatment of materials, which method does not demonstrate the above-described defects. This and other objects have been attained by the device, tabletop and method and use of device and method as described below.

Figure 9:
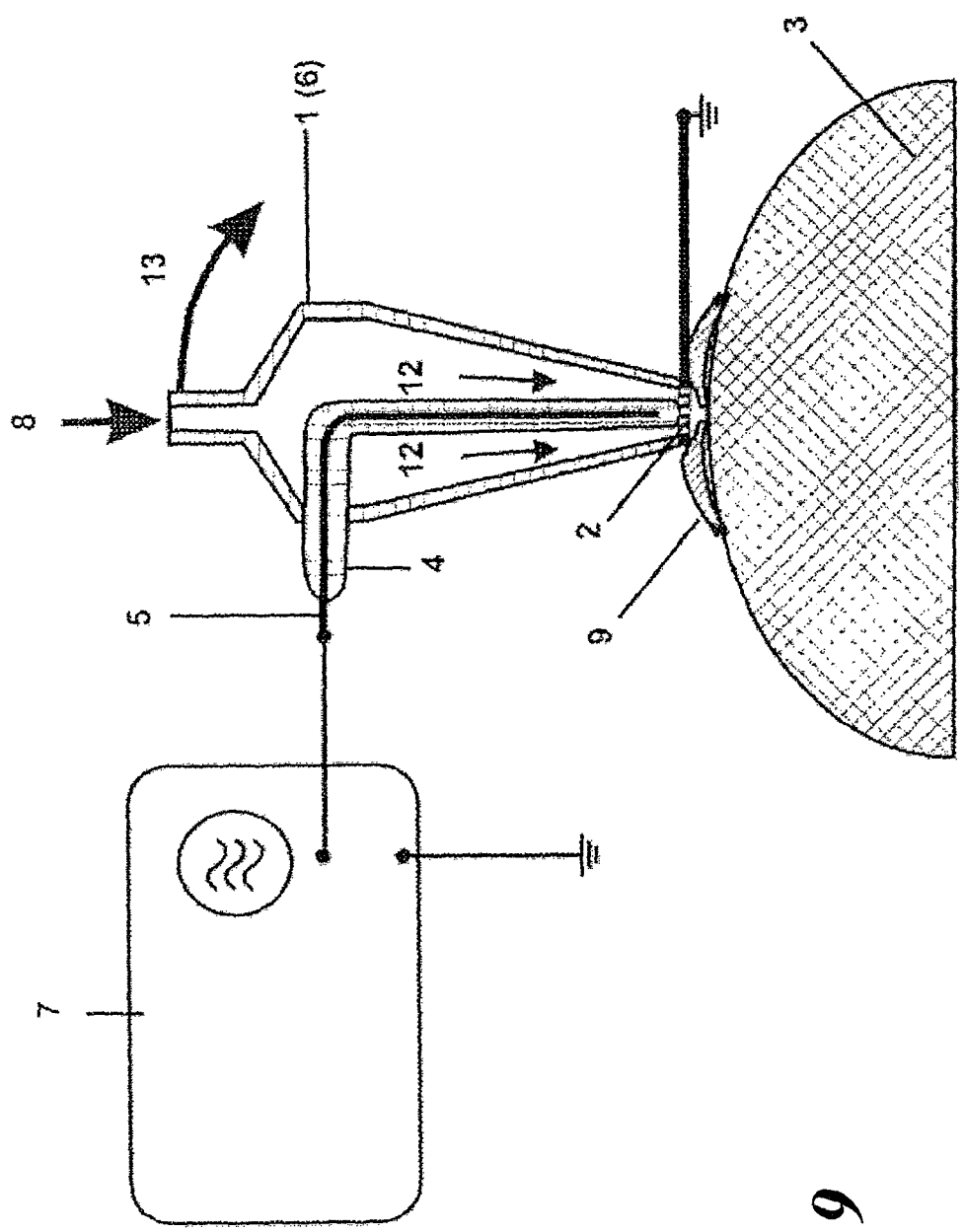
FIG. 9 demonstrates the fundamental structure of a compact hand-held device for treatment of plastic surfaces having a complex shape, in which the high-voltage electrode (5), covered with an insulator (4), is disposed in the gas nozzle (1). At the end of this high-voltage electrode, the electrically conductive, grounded contact electrode (2), structured as a screen, is disposed in the plane of the nozzle opening.
Figure 10:
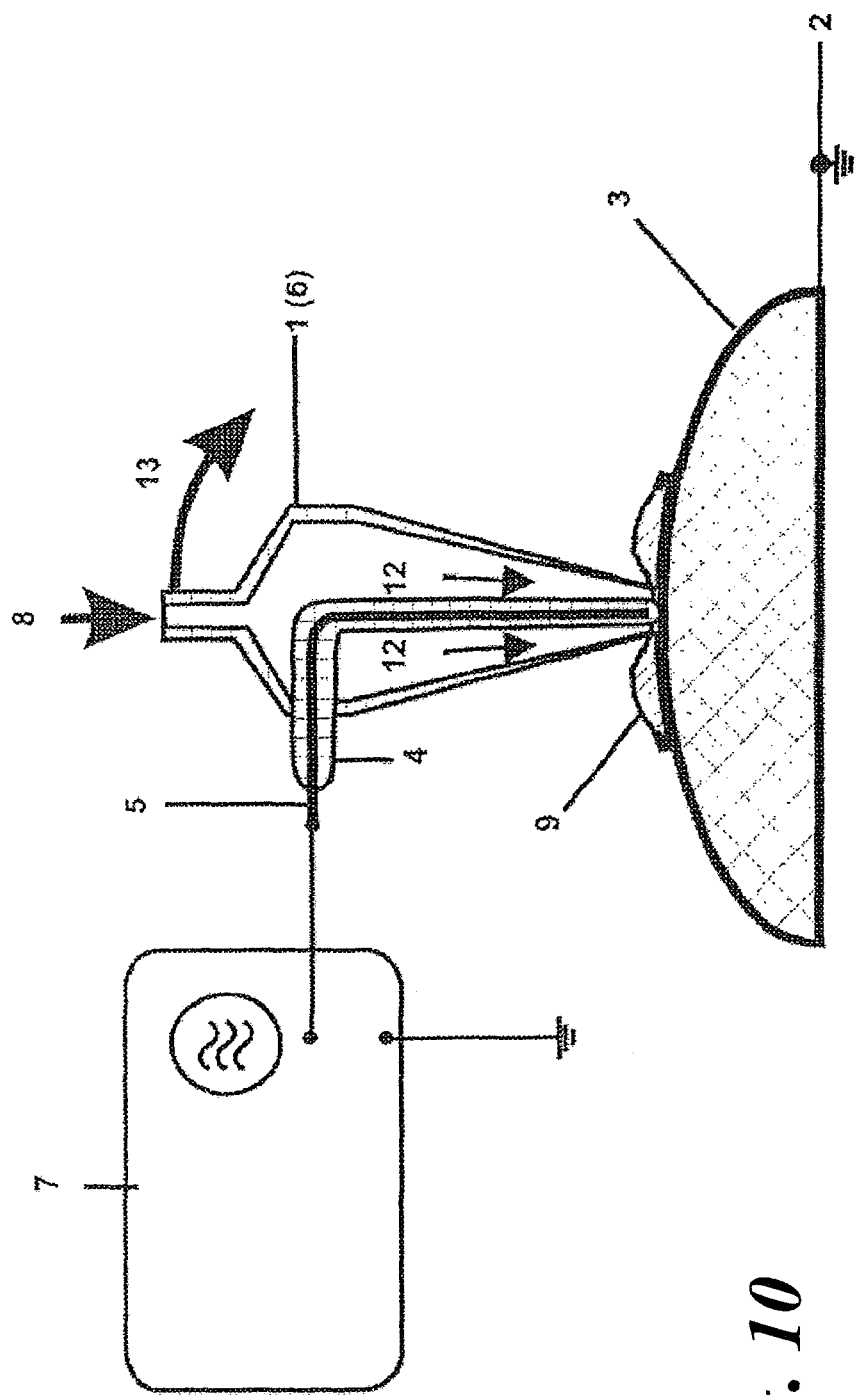

The arrangement shown in FIG. 10 has a similar design as that of FIG. 9. This device is intended for treatment of metal surfaces having a complex shape. Since, in this case, the metal surface itself serves as a conductive, grounded contact electrode, it is possible to do without a special contact electrode mounted on the nozzle.

Figure 11:
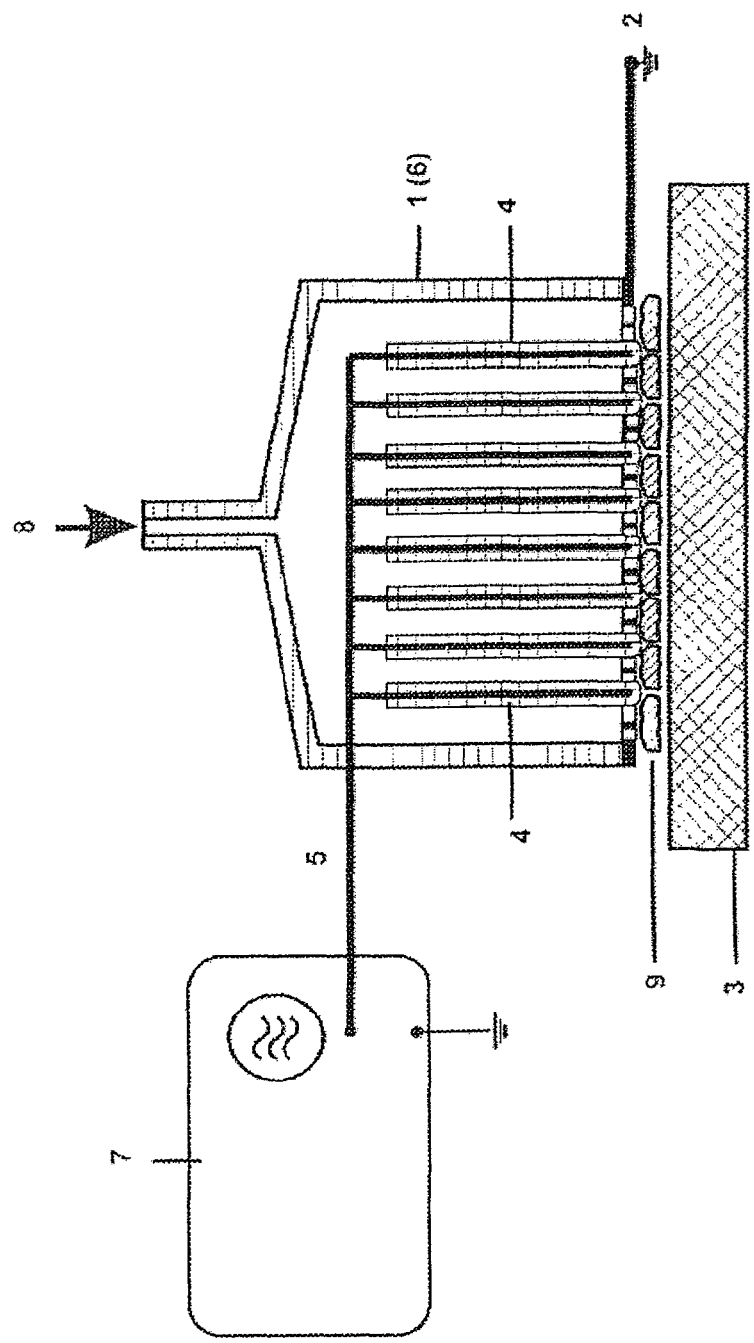

FIG. 11 shows another embodiment of a compact hand-held device, in which an array of multiple individual electrodes is used in place of a single insulator-covered high-voltage electrode. In this manner, surface discharges having a greater area expanse are produced, so that the required treatment times can be reduced accordingly.

Figure 12:
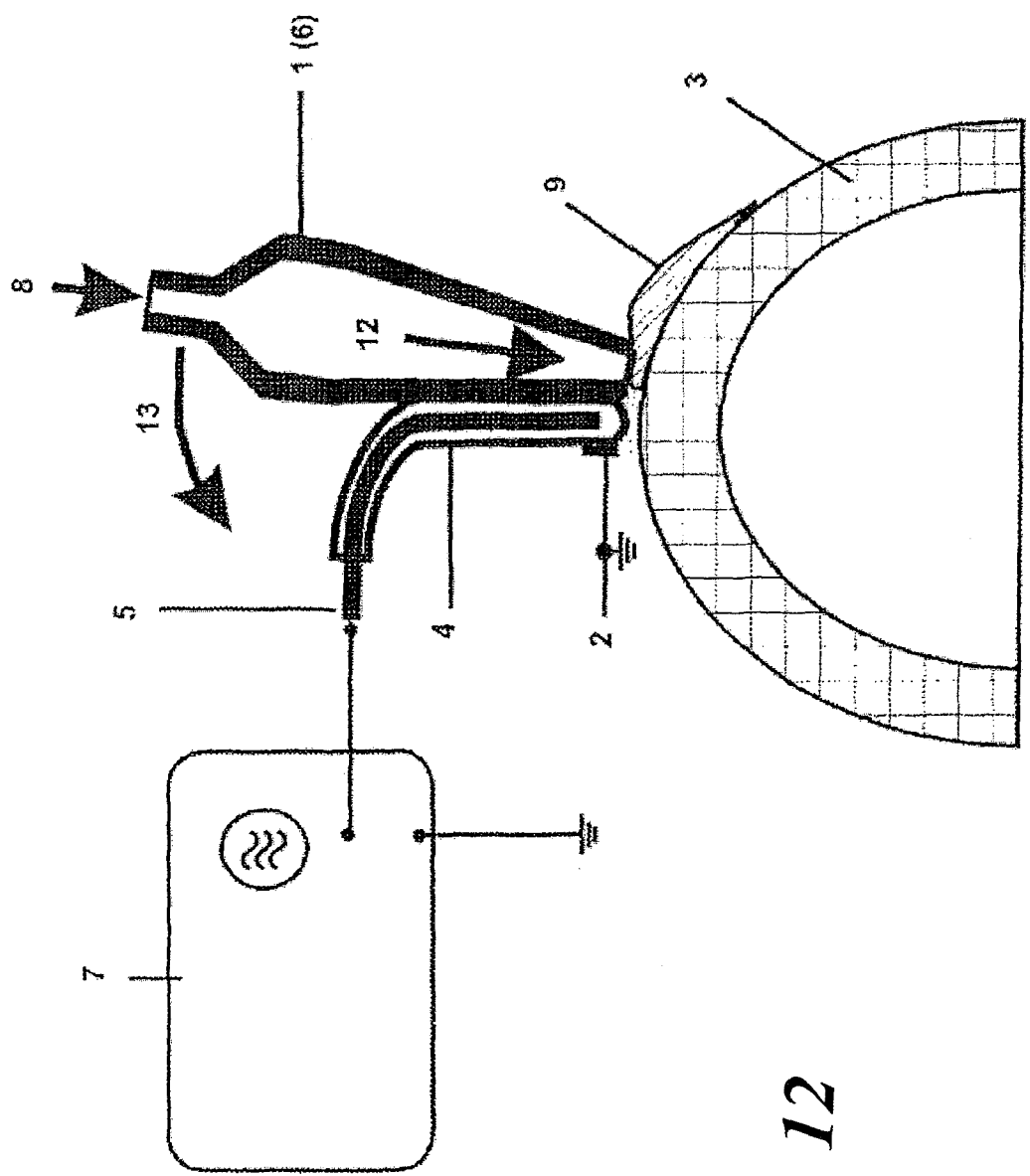

FIG. 12 shows an arrangement in which the high-voltage electrode (5) surrounded by a dielectric (4) can also be disposed outside of the gas nozzle.

Figure 13:
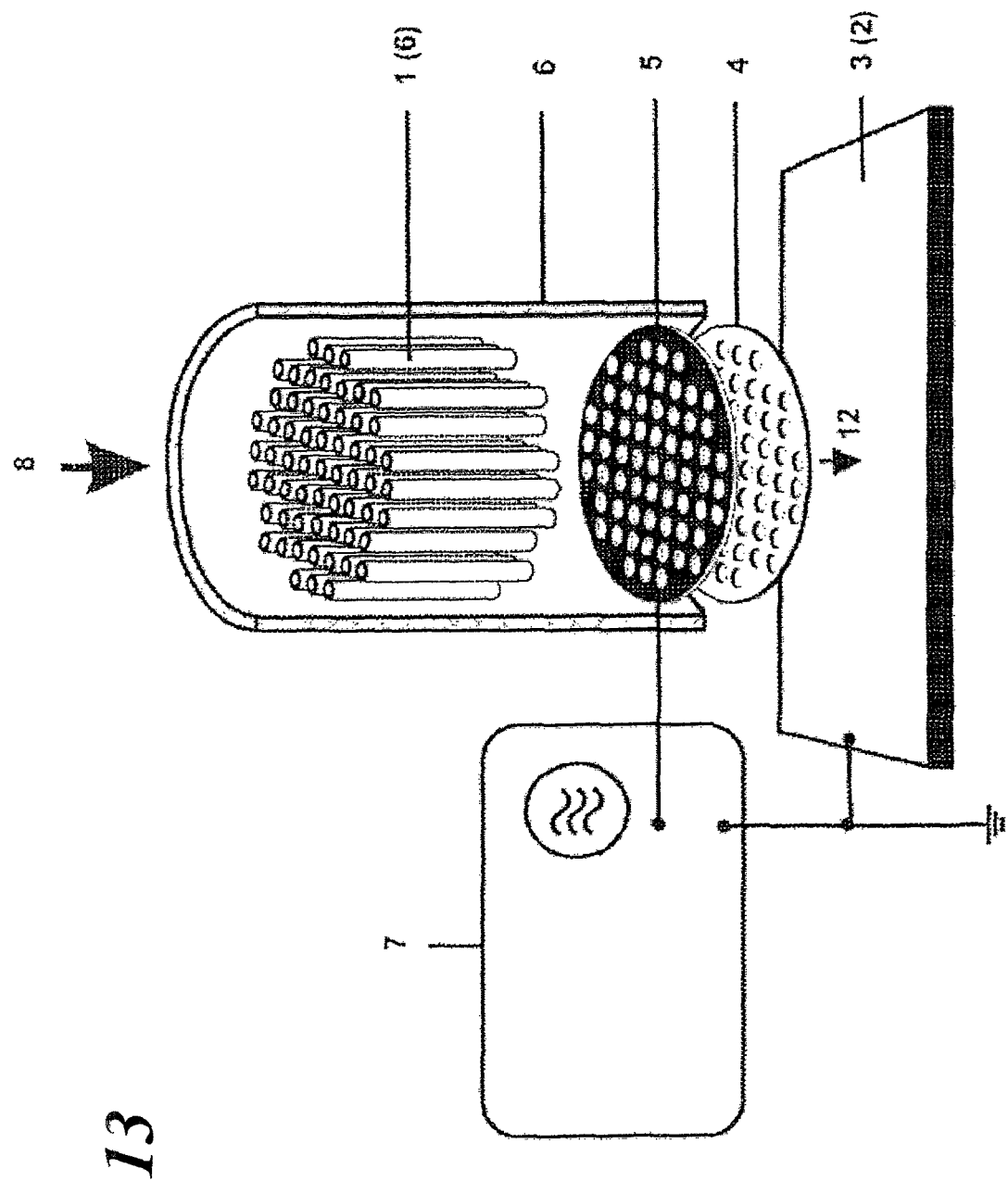
Figure 14:
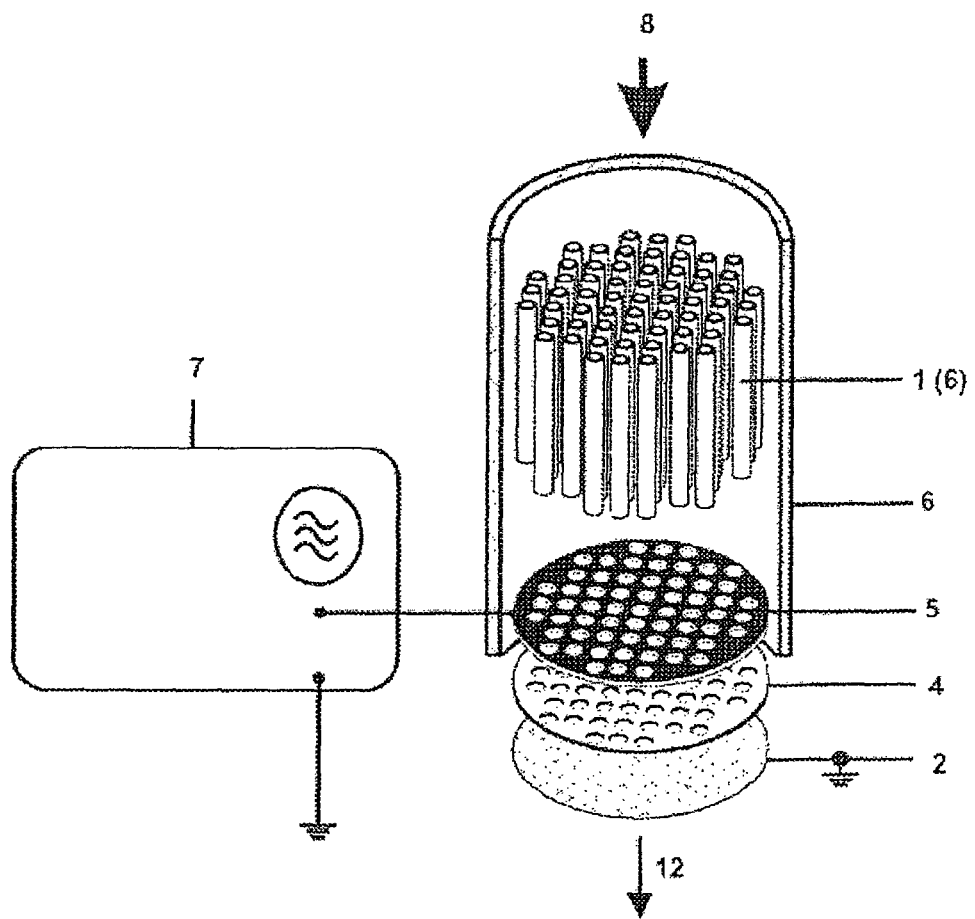
Figure 15:
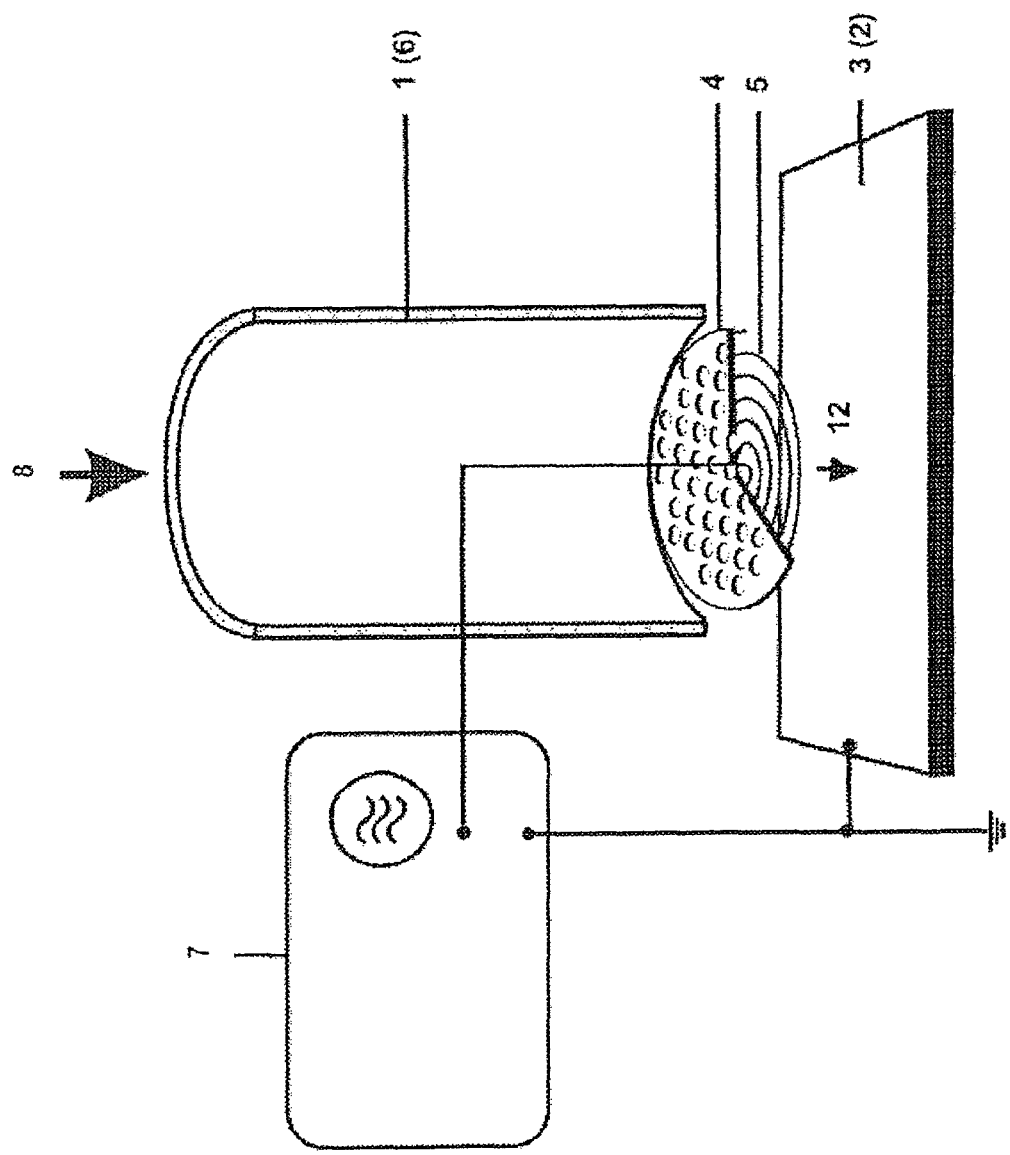

FIG. 13 to FIG. 16 show other design examples of compact hand-held devices. The arrangement according to FIG. 13 is an embodiment for treatment of metal surfaces, structured as a compact multi-channel plasma nozzle, in which the metallic work piece functions as a grounded contact electrode, and that of FIG. 14 is a similar arrangement for treatment of plastic surfaces, with a metal gauze disposed in the plane of the nozzle openings as a grounded contact electrode (2). In the embodiments shown in FIG. 15 and FIG. 16, the process gas flows through a perforated plate made of insulation material (6), in front of which the insulator-covered high-voltage electrode (4/5) is disposed. FIG. 15, in a manner similar to FIG. 13, shows the case for treatment of metal surfaces (acting as a grounded contact electrode), and FIG. 16, in a manner similar to FIG. 14, shows the case of treatment of plastic surfaces (metal gauze as a grounded contact electrode).

Figure 17:
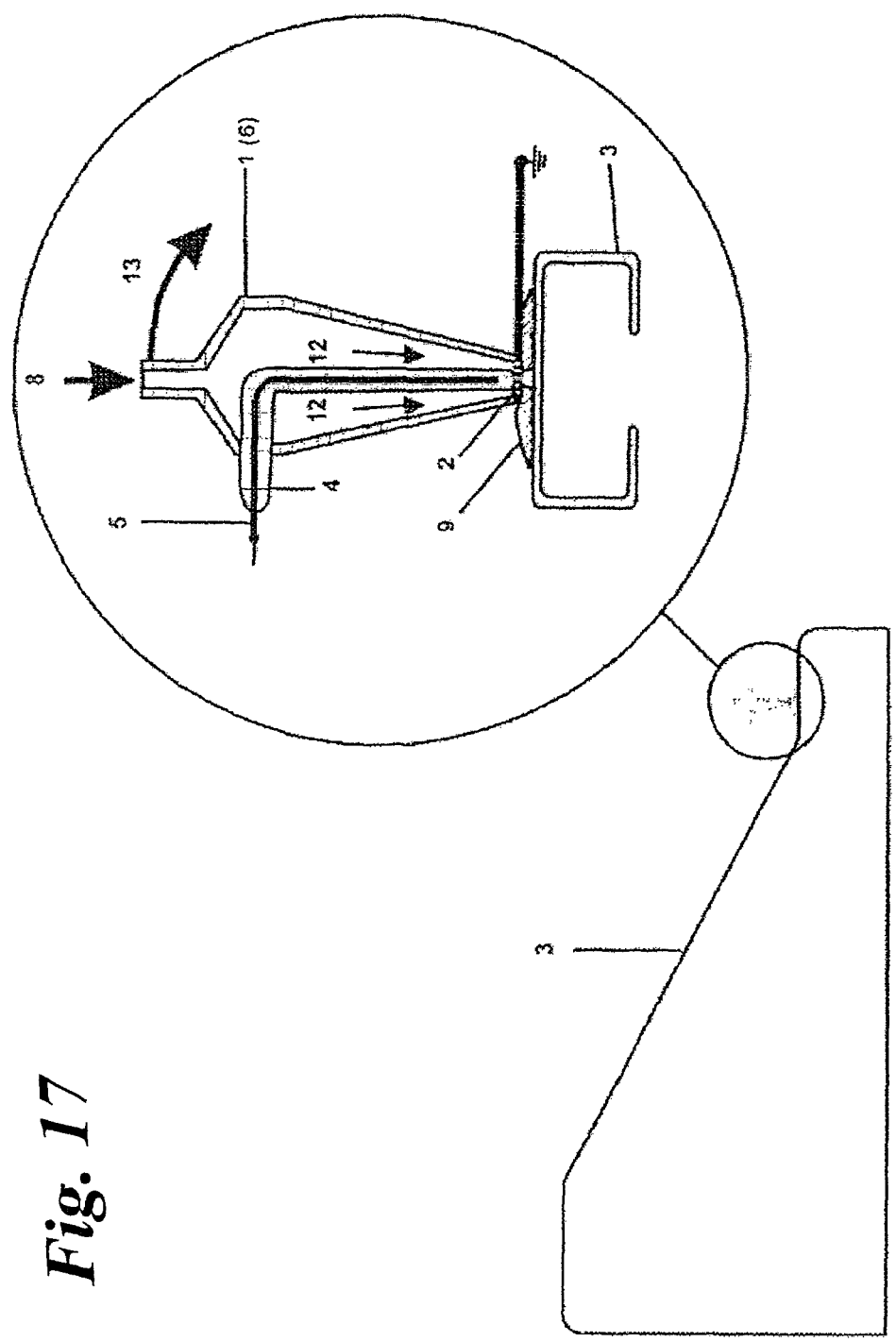

FIG. 17 shows the possibility of using a compact hand-held device as shown in FIG. 9 for dry cleaning and/or disinfection of handrails (3) (for example on escalators).

Figure 18:
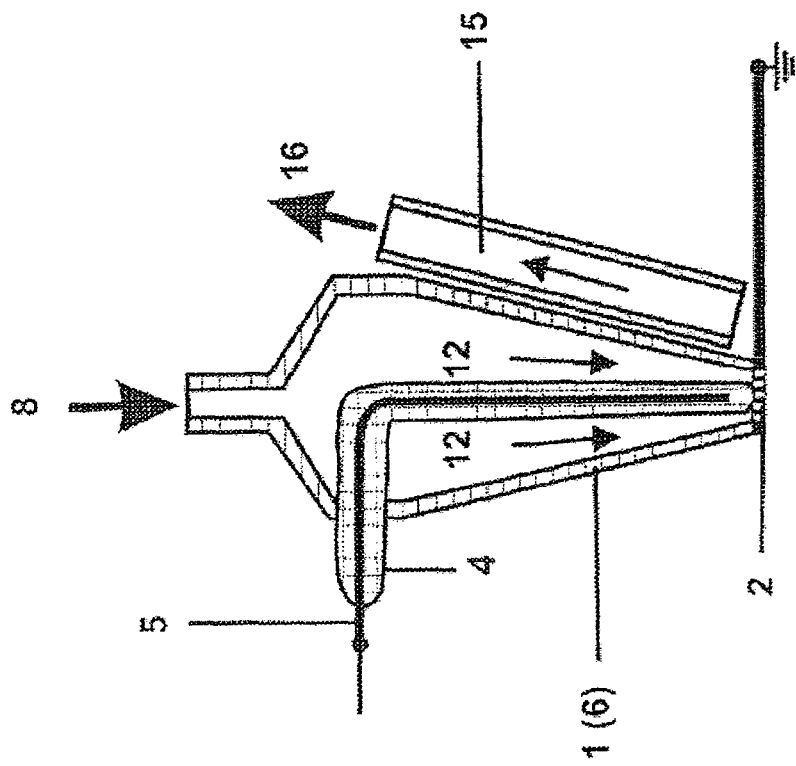
Figure 18:
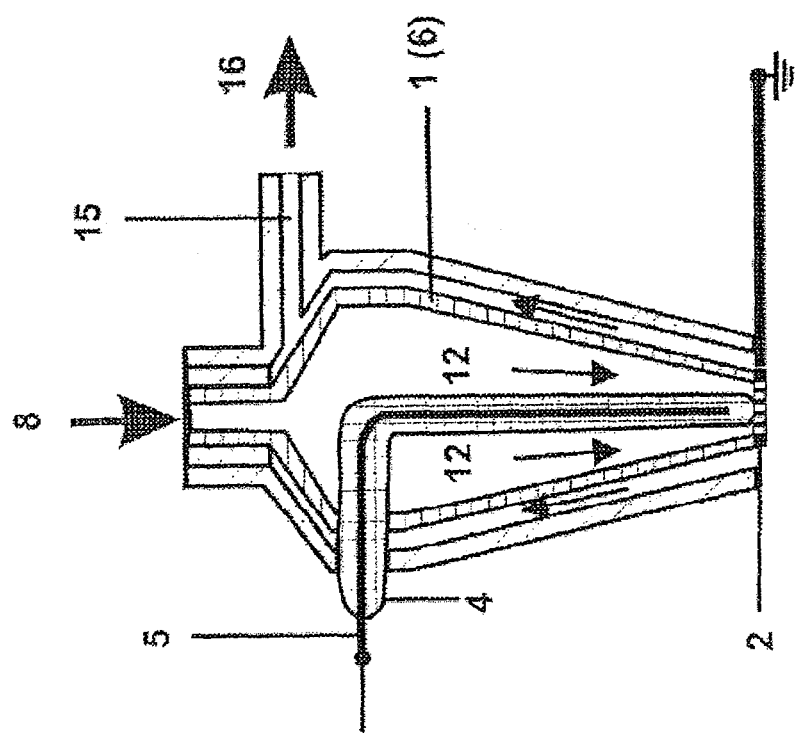

FIG. 18 shows two possibilities of placement of a second nozzle channel (15) for suctioning off (16) ozone that is produced by the discharge.

Figure 19:
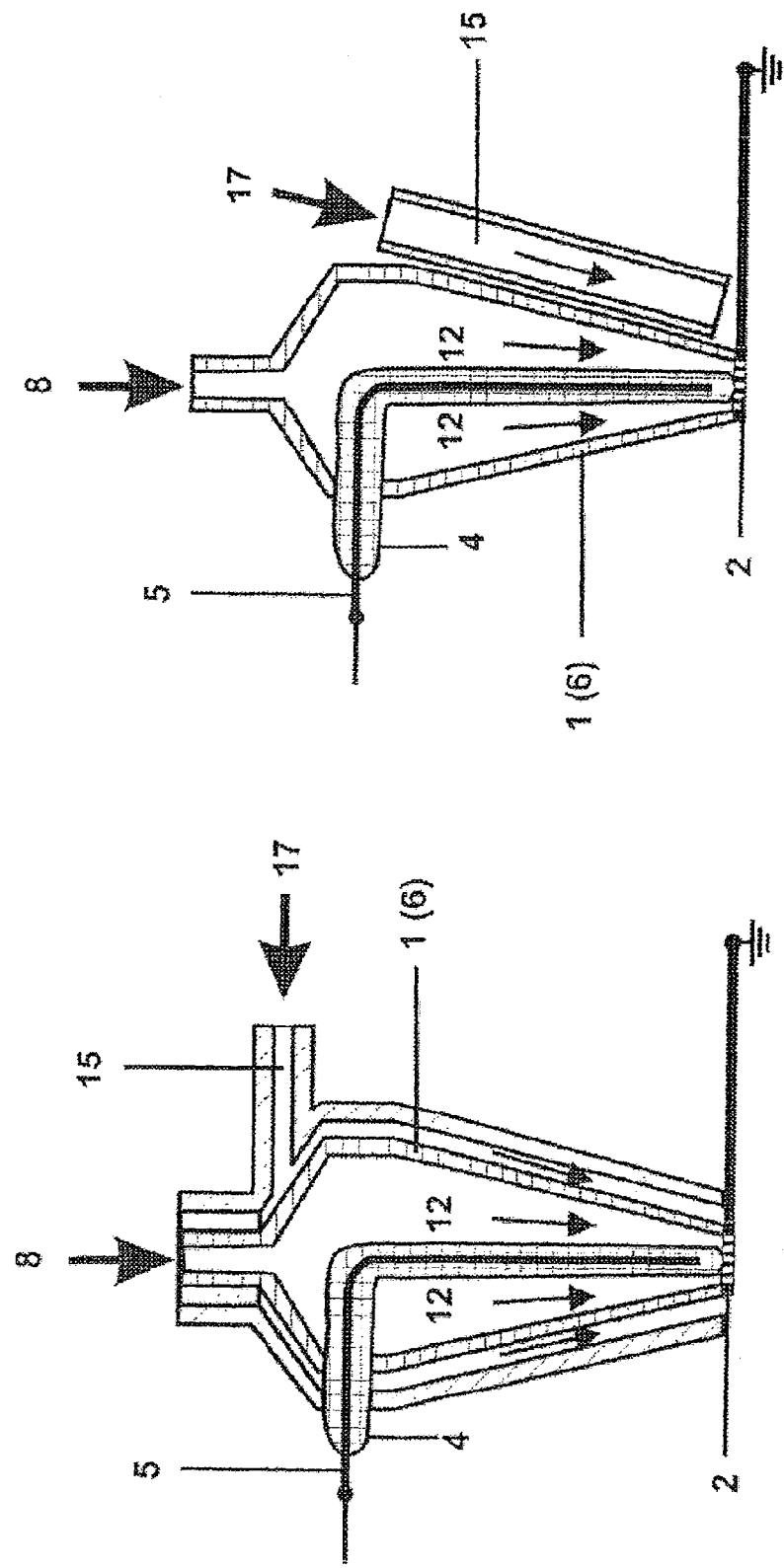

FIG. 19 shows that the nozzle channels (15) can also be used for the precursor feed (17) for the coating treatment.

Figure 20:
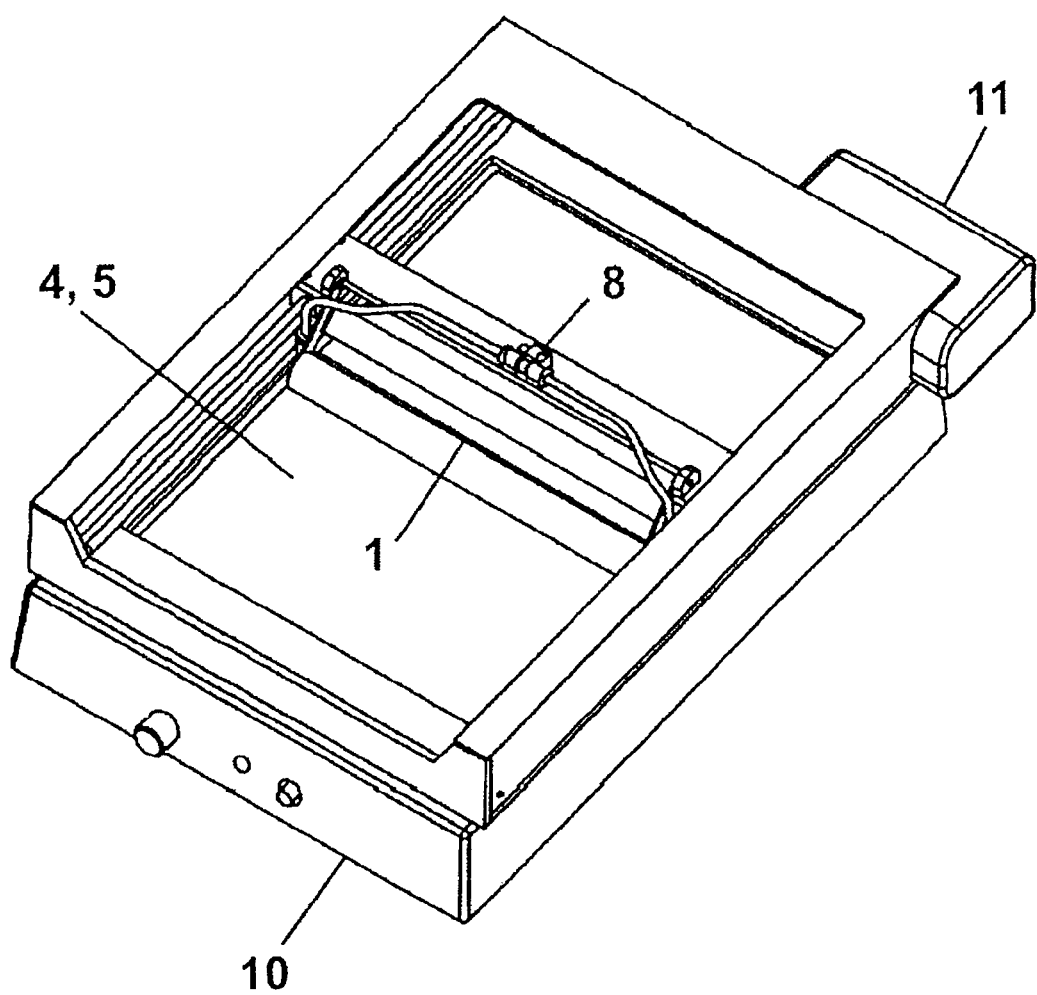

In FIG. 20, a motor-controlled tabletop device that functions according to the principle explained in FIG. 1 to FIG. 5 is shown.

Figure 21:
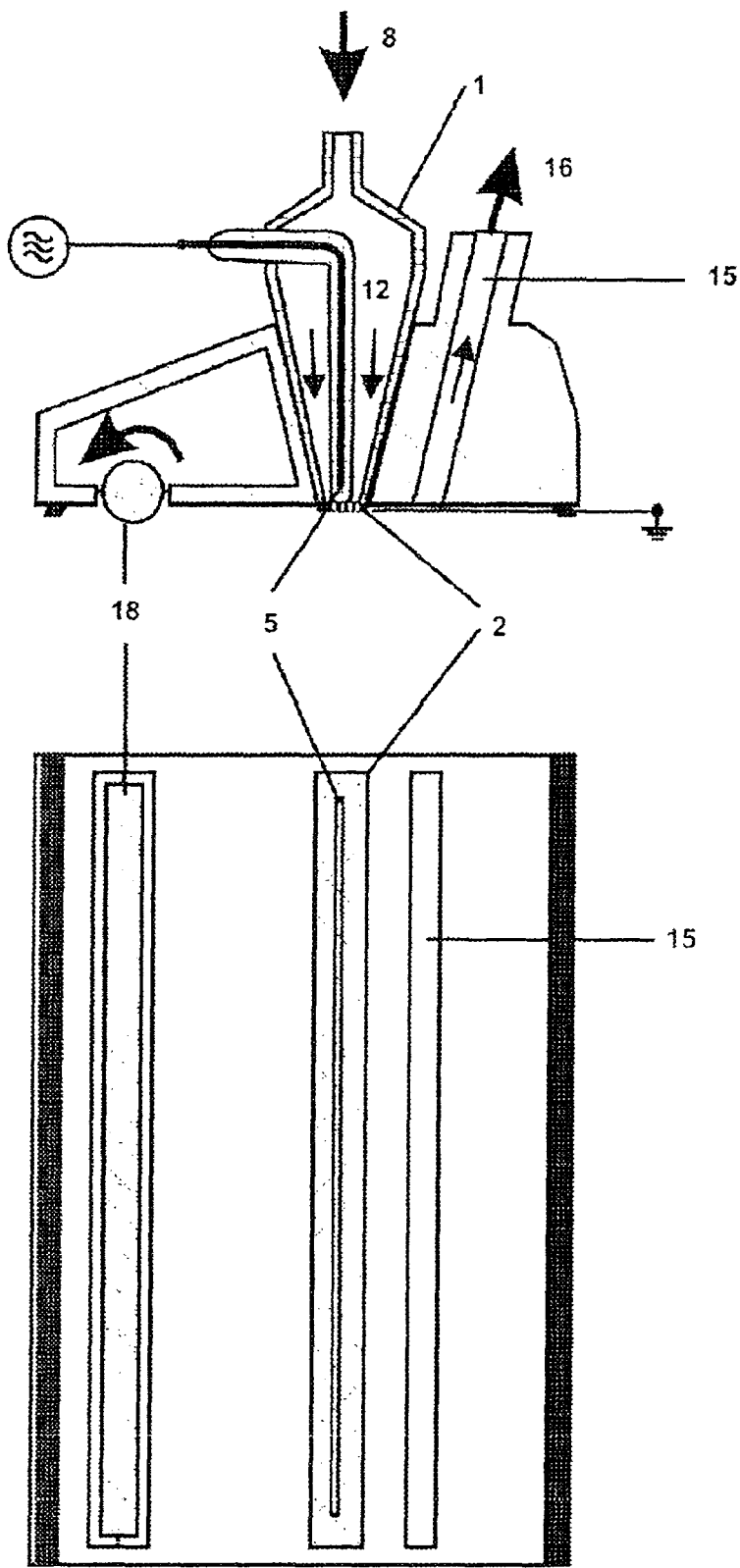

FIG. 21 shows, as another application example, a device for combined cleaning by means of a rotating brush (18), for dry cleaning and disinfection by means of plasma treatment by means of a device as shown in FIG. 9, and for suctioning off (16) dust and ozone by way of another nozzle (15).

Figure 22:
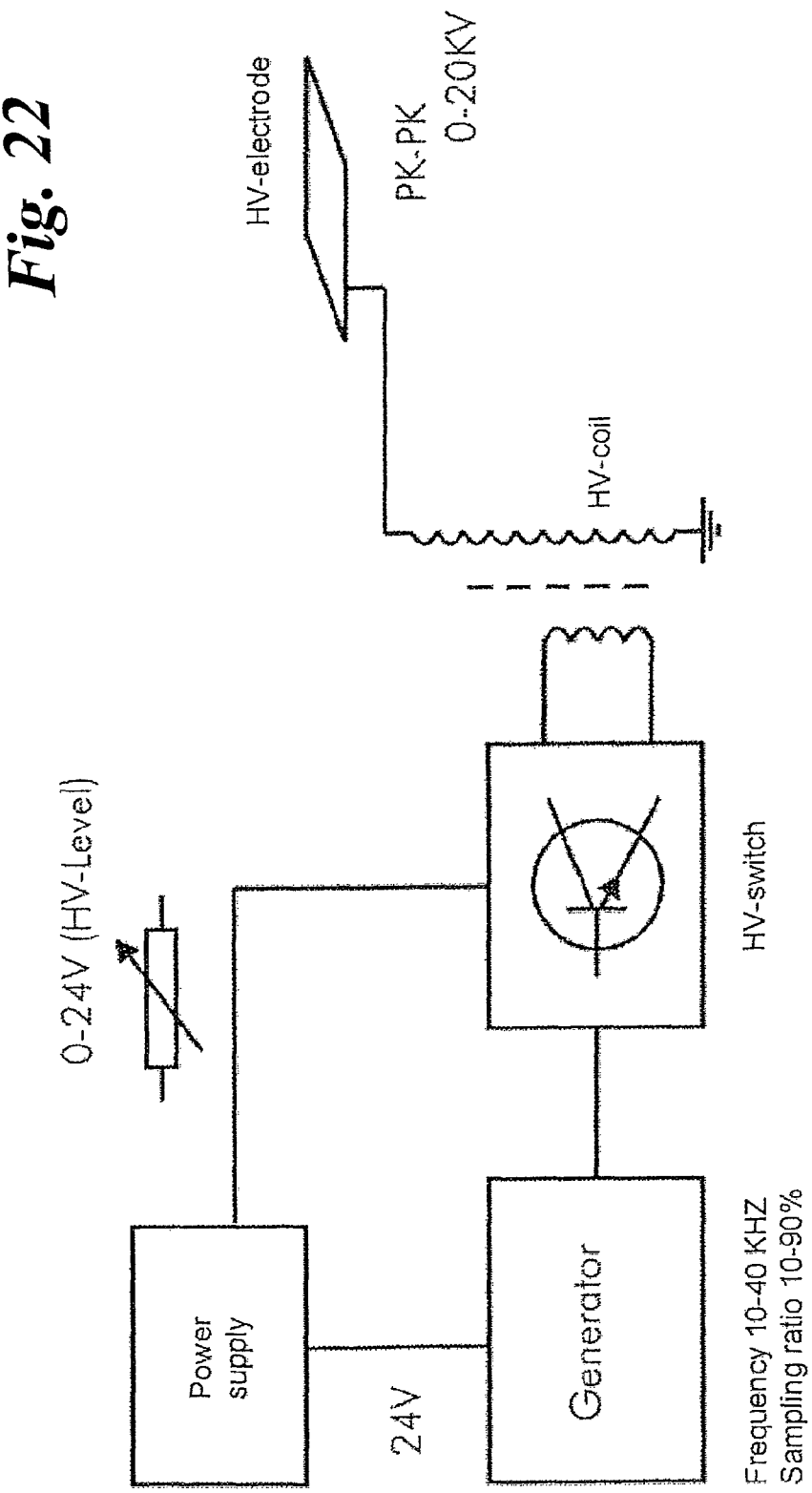

FIG. 22 shows the fundamental circuit schematic of the voltage supply.

Figure 23:
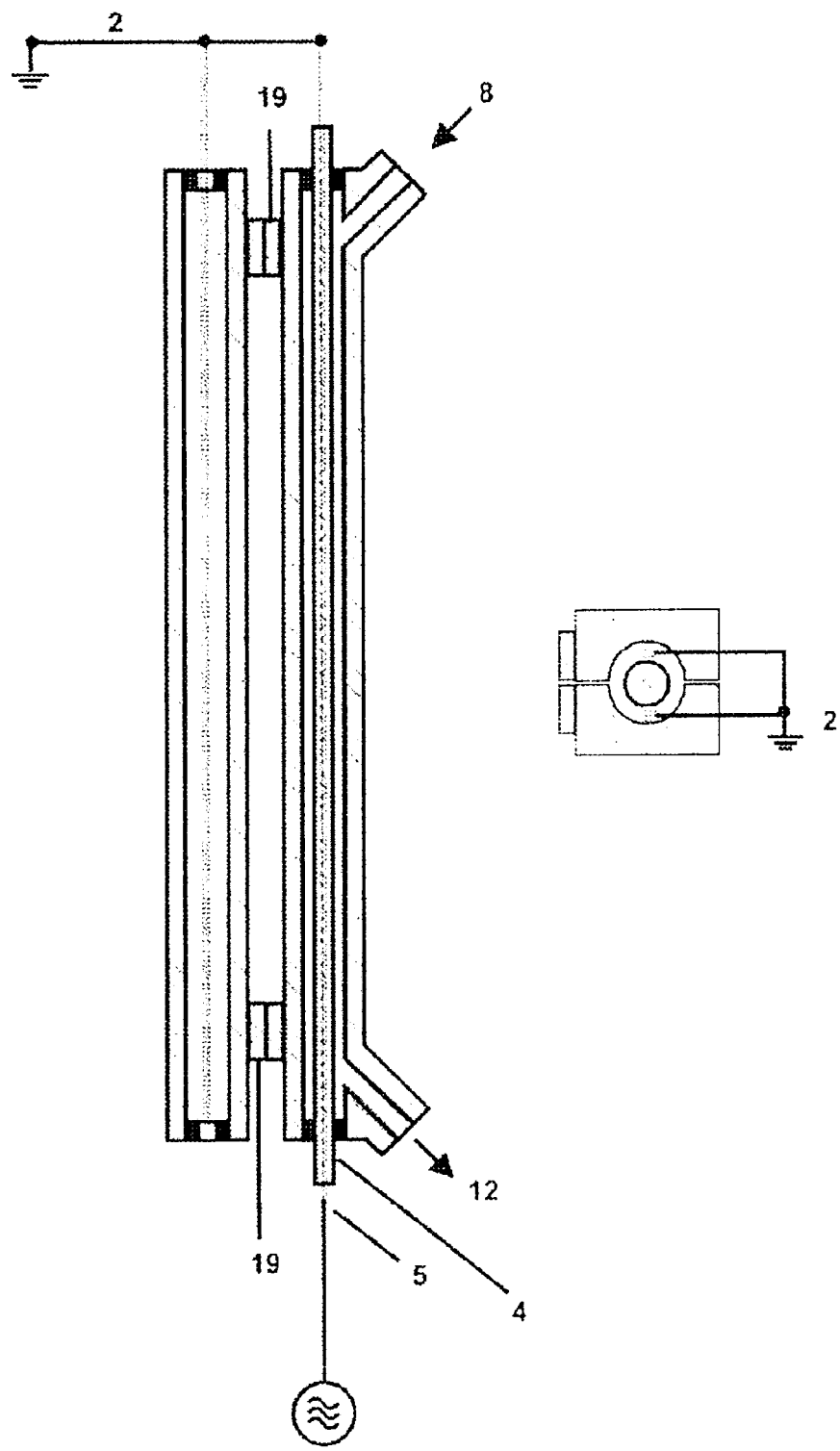

In FIG. 23, a treatment unit for external treatment of insulated wires to improve their wettability, which unit is based on the working principle of the invention, is shown.

Figure 24:
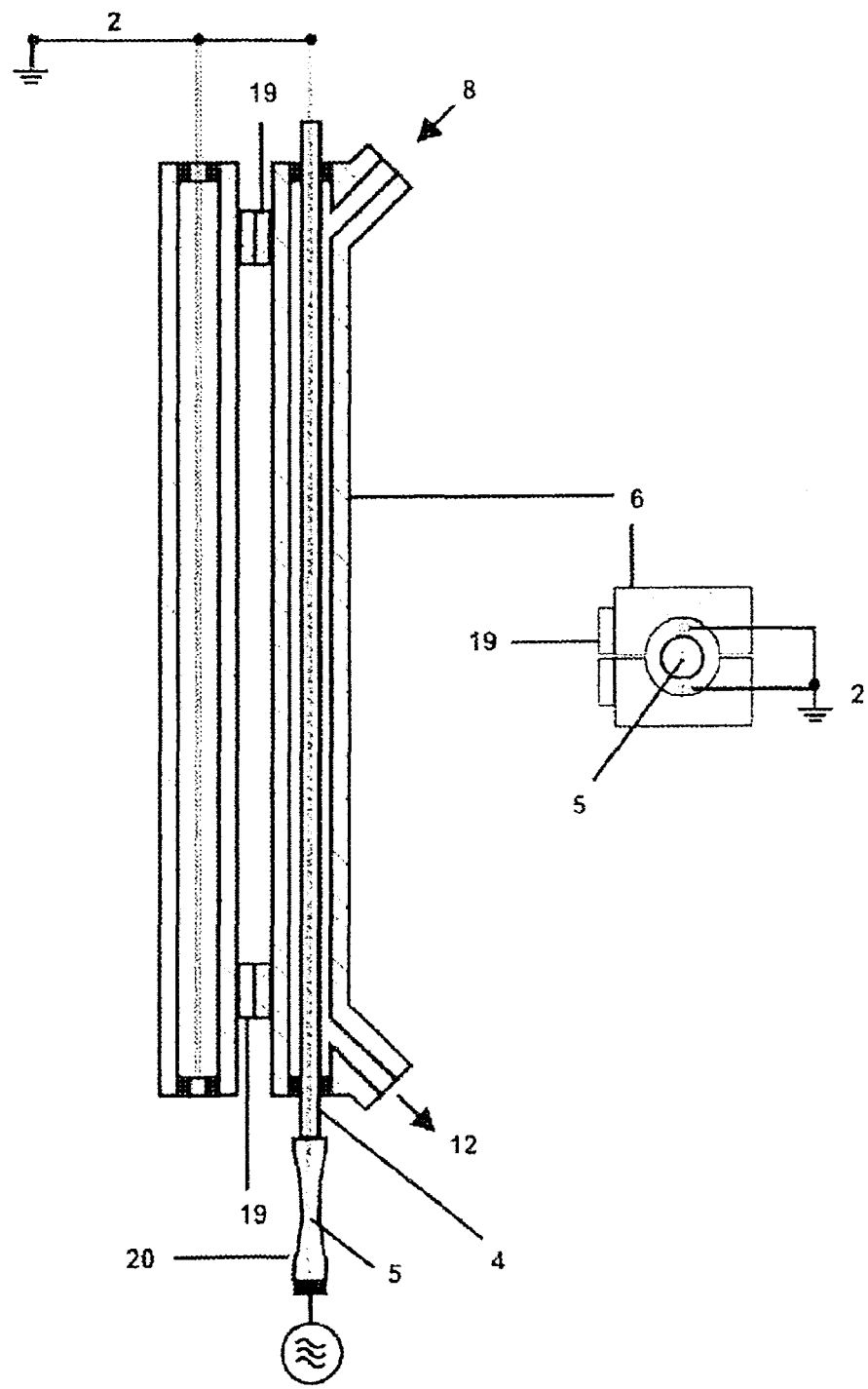

In FIG. 24, a treatment unit for dry cleaning and degerming of the outer surface of catheters, having a similar structure, is shown. In FIG. 23 and FIG. 24, the objects to be treated act as a high-voltage electrode (5) covered with a dielectric (4), and the electrically conductive, grounded contact electrode (2) consists of two thin wires that lie closely against the objects. A pipe of insulation material consisting of two halves that are connected by hinges (19) and can be opened up allows both holding and defined positioning of the objects, as well as precisely metered gas feed (8).

Figure 16:
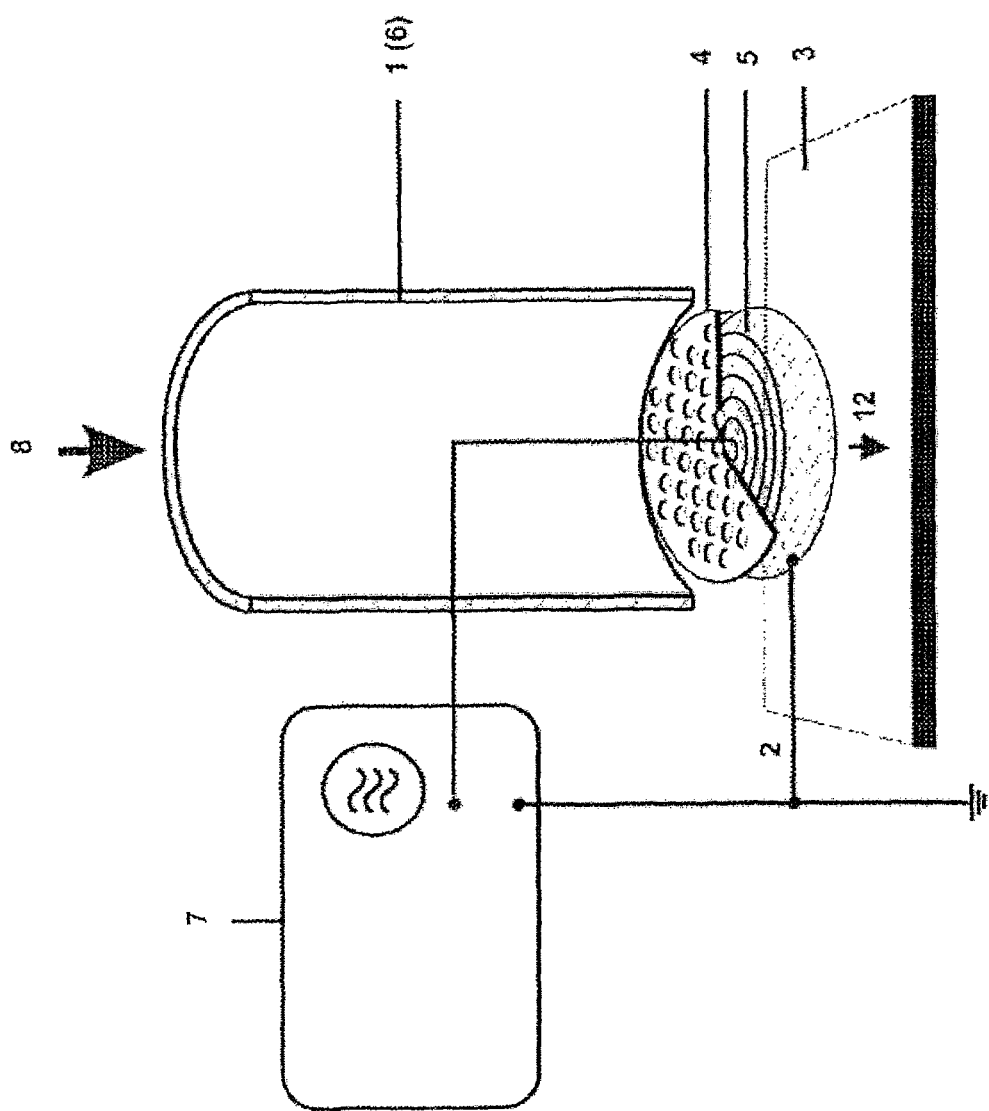
Figure 25:
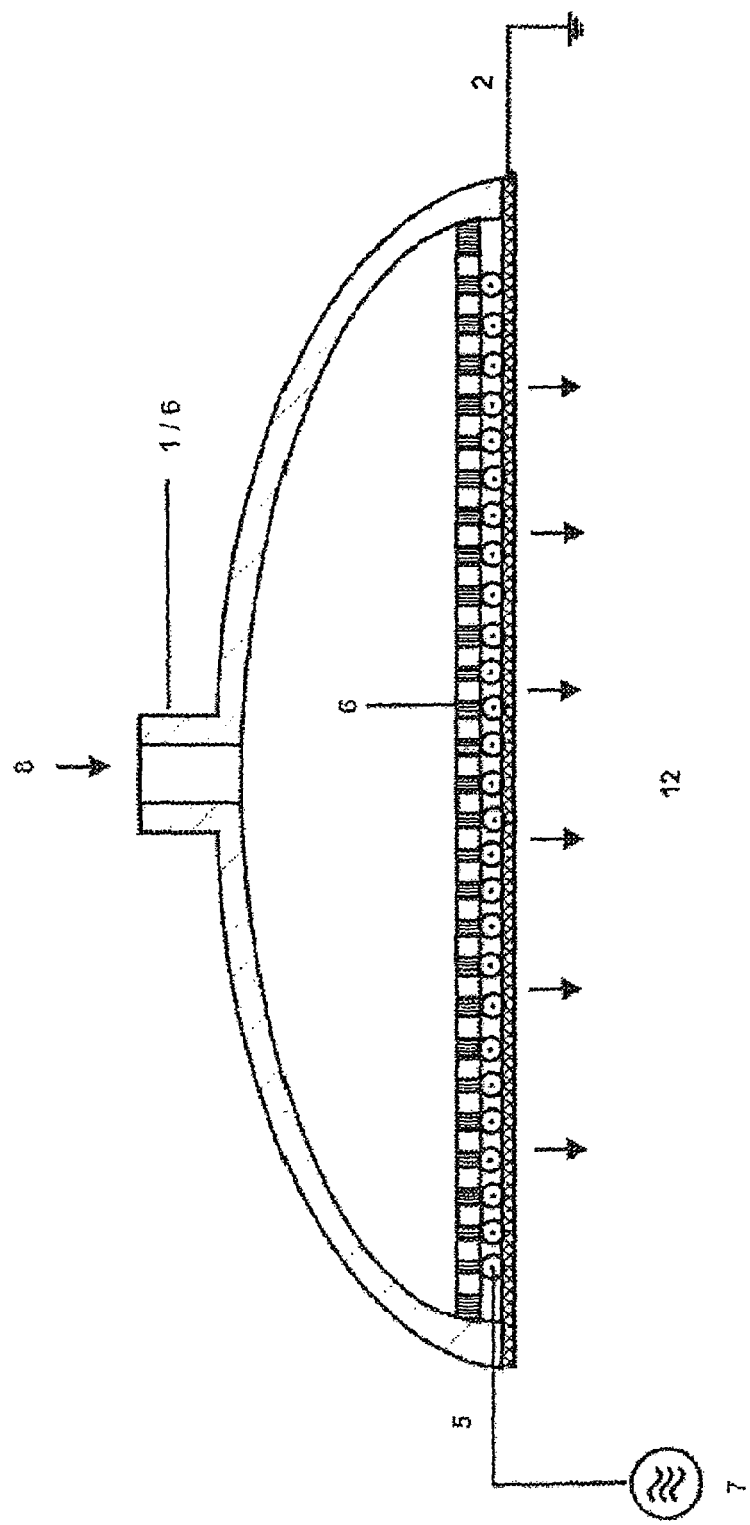

FIG. 25 shows a special embodiment of the arrangement shown in FIG. 16. In this case, the gas nozzle has a flatter shape and is produced from elastic materials, as are the electrodes and the gas-permeable insulation layer in the plane of the gas exit. This arrangement permits the contact surface to lie intimately against different body surfaces, and is thus fundamentally suitable for being laid onto regions of the human body, in the manner of an elastic cuff, with close skin contact, in order to be able to treat skin areas that might be diseased with it, by means of the surface discharge that is produced.

DETAILED DESCRIPTION OF THE PREFERRED EMBODIMENTS

In one embodiment, the invention relates to a method and a series of devices for dry cleaning, activating, modifying, coating, and biologically decontaminating (such as degerming, disinfecting, sterilizing) surfaces by means of an atmospheric pressure plasma generated using a surface barrier discharge. In one embodiment, the invention is used for dry cleaning, activating, coating, modifying, and biologically contaminating surfaces by means of an atmospheric pressure plasma generated in a defined, flowing gas atmosphere by a surface barrier discharge, comprising a high-voltage electrode that is covered with a dielectric or ferroelectric material, an electrically conducting grounded contact electrode, a high-voltage supply, a gas supply, and a gas nozzle (encompassing a gas outlet); said gas nozzle is located in the direct vicinity of the grounded contact electrode, is integrated into the contact electrode, or acts as the grounded contact electrode. Furthermore, the gas outlet is designed such that a discharged gas flow is directed to the contact point of the grounded contact electrode. The method is characterized in that the contact electrode including the gas nozzle and the material that is to be treated are moved relative to one another.

In one embodiment the present invention relates to a device for dry cleaning, activation, coating, modification, and biological decontamination of surfaces (3) by means of an atmospheric pressure plasma produced by means of a surface barrier discharge in a defined, flowing gas atmosphere, comprising a high-voltage electrode (5) covered by a dielectric or ferroelectric (4), an electrically conductive grounded contact electrode (2), a high-voltage supply (7), and a gas feed (8), a gas nozzle (1) with a gas exit opening (12), characterized in that
  a) the gas nozzle (1) is situated in the immediate vicinity of the grounded contact electrode (2), or
  b) the gas nozzle (1) is integrated into the contact electrode (2), or
  c) the gas nozzle (1) itself functions as a grounded contact electrode (2), and the gas exit opening (12) is designed in such a manner that an exiting gas stream is directed at the contact location of the grounded contact electrode (2).

An embodiment of the above device is characterized in that it additionally contains at least one of the following elements: insulation (6), a housing for the high-voltage supply (10), a motor, preferably having a magnetic clutch (11), joining edge (14), second nozzle channel (15), suction device (16), precursor feed (17), hinge (19) or handle piece with plug connector (20).

An embodiment of the above device is characterized in that a broad-jet nozzle functions as the gas nozzle (1).

An embodiment of the above device is characterized in that the broad jet nozzle has a slit having a width of 0.2-0.3 mm.

An embodiment of the above device is characterized in that a hand-held device having minimal geometric dimensions serves as the voltage source (7).

An embodiment of the above device is characterized in that the electrically conductive, grounded contact electrode (2) is structured as a slide contact or as a small roller, roll, brush, or whisk.

An embodiment of the above device is characterized in that the electrically conductive, grounded contact electrode (2) consists of metal or of other electrically conductive materials, preferably electrically conductive elastomers.

An embodiment of the above device is characterized in that the surfaces (3) to be treated are used as a dielectric-covered high-voltage electrode (5).

An embodiment of the above device is characterized in that the dielectric-covered high-voltage electrode (5) is configured as a planar mold or as a rotating roller.

An embodiment of the above device is characterized in that the surface (3) is surrounded by an electrically conductive mold and this mold forms the dielectric-covered high-voltage electrode (5).

An embodiment of the above device is characterized in that it represents a compact hand-held device in which one or more insulator-covered high-voltage electrodes are integrated into the hand-held device, together with a grounded contact electrode formed from a metal gauze or a perforated metal sheet, and are disposed in the plane of the gas exit from the gas nozzle, so that in this region, an intensified surface discharge is produced on the surface of the dielectric of the high-voltage electrodes.

In another embodiment the invention relates to a tabletop device for the treatment of planar materials having a restricted area expanse, which contains the above device.

An embodiment of the above tabletop device is characterized in that scanning of the surface, similar to an optical scanner, takes place by way of a motor drive.

In yet another embodiment, the present invention relates to a method for dry cleaning, activation, coating, and biological decontamination of surfaces by means of the above device, comprising:
  a) a material (3) to be treated is situated either between the high-voltage electrode (5) covered with a dielectric or ferroelectric (4) and the grounded contact electrode (2), or at their contact location,
  b) a process gas stream is directed out of the gas nozzle (1) onto the contact location of the grounded contact electrode (2),
  c) at the same time or immediately afterward, a voltage is applied to the high-voltage electrode (5), and
  d) the contact electrode (2) with the gas nozzle (1) and the material (3) to be treated are moved relative to one another,
whereby a surface barrier discharge is produced in the process gas stream on the surface of the material (3) to be treated, on which the contact electrode (2) with the gas nozzle (1) is situated, or in its immediate vicinity.

An embodiment of the above method is characterized in that a noble gas, preferably argon, is used in pure form or as a mixture with other gases.

An embodiment of the above method is characterized in that the material (3) to be treated is laid onto an insulation material layer of the planar, dielectric-covered or ferroelectric-covered high-voltage electrode (5), and the electrically conductive, grounded contact electrode (2), coupled with a broad-jet gas nozzle (1), is guided to slide over the plastic surface to be treated.

An embodiment of the above method is characterized in that for the treatment of planar materials having a restricted area expanse (for example in the formats DIN A6 to DIN A0), in which scanning of the surface takes place similar to an optical scanner, by way of a motor drive.

An embodiment of the above method is characterized in that for advantageous treatment of longer web materials or plates, in which a dielectric-covered or ferroelectric-covered high-voltage electrode configured as a rotating roller instead of as a planar electrode is used, and the material to be treated is moved through between the rotating high-voltage electrode and the broad jet gas nozzle configured as the grounded contact electrode, which slides or rolls on the surface of the material, by means of a suitable advancing device.

An embodiment of the above method is characterized in that hollow bodies made of plastic are treated, in that the hollow bodies are filled with a conductive mass (for example with steel wool, conductive plastic material or with electrically conductive fluid), which mass is connected with the high voltage and thus acts as a dielectric-covered high-voltage electrode, together with the hollow plastic body.

An embodiment of the above method is characterized in that for dry cleaning and/or biological decontamination of the inner surface of bottles, the bottle is surrounded by two halves of an electrically conductive mold, with precise fit, to which halves high-voltage potential is applied, which mold, together with the bottle wall, acts as a dielectric-covered high-voltage electrode, and in the interior of the bottle, a bottle brush made of electrically conductive material is disposed, having bristles that lie closely against the inner surface of the bottle, which acts as a grounded contact electrode, at the same time, and is coupled with a gas nozzle.

An embodiment of the above method is characterized in that for external treatment of insulated wires, in order to improve their wettability, the wires to be treated are used as a dielectric-covered high-voltage electrode and are disposed in a pipe made of insulation material, together with the electrically conductive, grounded contact electrodes, consisting of two thin wires, which lie closely against the wire to be treated.

An embodiment of the above method is characterized in that a precursor, preferably of silicon-organic compounds, such as HMDSO or TEOS, is added to the process gas, directly or by way of a second nozzle, in order to produce $SiO_x$ layers, for coating of inner and outer surfaces.

An embodiment of the above method is characterized in that a continuous or pulsed alternating voltage, pulsed direct voltage, or individual high-voltage pulses are used as the high-voltage, preferably an alternating voltage as a sine, rectangle, or triangle function.

The invention also relates to the use of a device a described above or of the method as described above for
  a) treatment of surfaces in operating rooms or
  b) treatment of surfaces in the foods sector or
  c) treatment of metal surfaces or
  d) treatment of plastic surfaces or
  e) cleaning and disinfection of stair handrails or
  f) removal of parting agent residues from surfaces or
  g) external treatment of insulated wires or
  h) dry cleaning, disinfection, and biological decontamination of hoses used in medical devices or instruments or
  i) treatment or coating of the inner surfaces of pipes or hoses or
  j) healing of skin diseases or
  k) treatment of biological tissue, particularly wounds, or
  l) plasma treatment of films or signs made of plastic, particularly to improve the adhesion of adhesive films or printing inks on these materials.

All ranges described below explicitly include all values and subvalues between the upper and lower limit of the range.

According to the invention, a device and a method for treatment of surfaces is made available, for the first time, which are characterized in that a surface barrier discharge is provided on the surface of the material to be treated, or in an immediate vicinity of the surface, by means of contact of a dielectric-covered high-voltage electrode with a grounded, electrically conductive contact electrode, which is operated in a weak process gas atmosphere that flows out of a specially adapted gas nozzle and is directed locally onto the contact location. In this connection, the directed, weak process gas stream plays a significant role for the efficiency of the device for surface treatment, and thus for the overall function. If one uses a noble gas, such as argon, for example, for this purpose, the ignition voltage of the surface discharge is clearly reduced as compared with operation in air, and the light phenomena of the plasma on the surface of the insulation material (dielectric) riot only becomes brighter, but also covers a greater area of the material. This visual appearance is connected with a clearly stronger effect of the surface treatment by the plasma, as can be proven by means of contact angle measurements and suitable methods of surface diagnostics, for example. In this connection, a very small gas flow is sufficient to achieve this effect. For example, it is already possible to achieve a clear effect with a grounded contact electrode having a length of 20 cm and a broad jet nozzle disposed next to it, having the same length, from which the gas flows onto the contact location through a slit having a width of approximately 0.2-0.3 mm, at a gas flow of 0.5-1 slm (slm—standard liters per minute) Ar. The advantages of the surface barrier discharges used here as compared with so-called volume barrier discharges, which primarily consist in that both the required operating voltages and the electrical power used are lower, and the plasmas have a more homogeneous structure, are significantly intensified by means of the precisely metered feed of this gas stream, so that the requirements regarding the power supply devices can be clearly reduced.

As an important component of one embodiment of the device, the power supply device can therefore be dimensioned with minimal geometric dimensions, so that it can be integrated into a device structured as a hand-held device, for example. In this connection, the voltage supply of the high-voltage electrode takes place by means of rapid switching of a high-voltage transformer. The switching signal required for this, with a frequency of 10 kHz to 40 kHz and a variable sampling ratio of 10 to 90%, is supplied by a square-wave generator. The actual switching stage consists of a power MOSFET with a driver circuit switched ahead of it. The high-voltage amplitude can be regulated up to a maximal value of 7 $kV_{eff}$.

Surprisingly, it has been found that the device according to the invention can be operated without cooling, at a low energy and gas consumption, and with a simple, cost-advantageous power supply device, that it allows uniform, efficient treatment without damage to the material to be treated, that it is suitable even for treatment of work pieces having a complex surface geometry, and that it offers the possibility of being used as a hand-held device, for manually guided operation. The properties of the device point to areas of application that go beyond its use for surface treatment of work pieces. For example, treatment of biological tissue is possible in the case of a corresponding embodiment.

Depending on the type, shape, and size of the materials to be treated, and on the desired treatment effect, the structure and placement of the dielectric-covered high-voltage electrode, the grounded contact electrode, and the gas nozzle can be structured and/or combined in different ways. For example, in a basic structure for treatment of plastics in the form of planar film, web, or plate materials, the material to be treated can be laid onto the insulation material layer of a planar, dielectric-covered high-voltage electrode. The electrically conductive, grounded contact electrode, coupled with a broad jet gas nozzle, is guided over the plastic surface to be treated. In this connection, the contact electrode can be structured both as a slide contact and as a roller or brush, and can be made either from metal or from other electrically conductive materials (for example, from electrically conductive elastomers). The exit opening of the broad jet gas nozzle, which is configured as a narrow slit, is disposed directly next to the contact strip of the contact electrode. If a voltage of sufficient intensity (depending on the type and thickness of the material) is applied to the high-voltage electrode, then a surface discharge begins at the contact strip, on the plastic surface. The expanse of this discharge is increased in size, and its intensity is significantly increased, by means of the weak gas stream that impacts the contact strip from the slit of the broad-jet nozzle.

The electrode array is always structured in such a manner that the electrodes are situated on or in the immediate vicinity of the work piece, and the plasma is produced directly at its location of effect, if possible. The gas stream used does not have the function of carrying the plasma out of the electrode array to the work piece or to cool the electrode array, as in the case of plasma jets, but rather serves merely for local intensification of the plasma at its location of effect and for control of its parameters (including type and condition of the excited species). The gas consumption is kept very low by means of the special electrode array, and the ignition voltage required for plasma operation is minimized. As a result, the required power supply devices can be configured to be very small, simple, and compact.

Furthermore, particularly simple handling is possible, because for one thing, it is not necessary to keep a specific distance between plasma source and surface to be treated, and for another, this distance does not have to be ensured by means of complicated positioning systems, but rather the discharge is simply guided over the surface to be treated, in the form of a mobile contact plasma. Such devices can be used universally, on any desired work pieces. Furthermore, because of the fundamental differences in structure, it is always possible to produce a so-called cold plasma, i.e. the gas temperature is raised only slightly, as experience has shown, in contrast to the plasma jets described in the state of the art, which convert a not insignificant part of the electrical energy coupled in into heat, due to the initial production of an arc, as experience has shown.

In the invention described here—in contrast to the devices and methods named in the background art—the discharge electrodes mantled by dielectric material are situated on top of or on the side of the work piece, which represents the counter-electrode, so that a so-called surface barrier discharge is produced directly on the surface to be treated. Thus, the discharge, as a mobile contact plasma, can simply be guided over the surface to be treated (hand-held device for manually guided operation), whereby the plasma formation on the surface is merely further intensified by an additional, but only slight or gentle gas stream (i.e., for example, no rotating or circulating guidance of the air stream). Since the gas stream no longer has to transport the plasma to the surface, the gas consumption is relatively slight. These differences allow very simple handling even for treatment of very complex work pieces, which is additionally supported in that because of the plasma intensification by means of the gentle process gas stream, the required power supply devices can be structured to be particularly small, simple, and compact.

In contrast to DE 102 19 197 C1, a method for external treatment of insulated wires, to improve their wettability, is presented with the invention described here. In this connection, the wires to be treated are used as high-voltage electrodes already mantled with a dielectric, and a surface barrier discharge is produced on the wire insulation surface by means of an electrically conductive, grounded contact electrode that lies closely against the insulated wire to be treated and is disposed in a pipe made of insulation material.

In accordance with the basic structure of this embodiment shown here, the device can be designed as a tabletop device for the treatment of planar materials having a restricted area expanse (for example in the formats DIN A6 to DIN A0 and all formats in between), in which scanning of the surfaces takes place, similar to the case of an optical scanner, by way of a motor drive. Devices of this type can advantageously be used, for example, in advertising studios or print shops, in order to achieve an improvement in the adhesion of adhesive films or printing inks on films or signs made of plastic, by means of plasma treatment of these materials.

As another application, this basic form of the device offers the possibility of implementing dry cleaning or disinfection (degerming, biological decontamination) for large surfaces in the clinical sector (for example in operating rooms) or in the foods sector, such as for specially prepared table or wall coverings, by means of this plasma treatment. For this purpose, the table or wall coverings must be configured in such a manner that they can be used as a dielectric-covered high-voltage electrode.

Another embodiment of the basic structure of the device presented above is obtained if a dielectric-covered high-voltage electrode configured to be a rotating roller is used in place of a planar electrode. Using such a device, web materials of longer plates can be treated, for example, in advantageous manner; these are moved through between the rotating high-voltage electrode and the broad jet gas nozzle configured as a contact electrode that slides or rolls on the surface of the material, by means of a suitable advancing device.

In another embodiment of this basic form of the device, hollow bodies made of plastic can be treated in that the hollow bodies are filled with a conductive mass (for example with steel wool, conductive plastic material, or with electrically conductive fluid), which mass is connected with the high voltage and thus acts as a dielectric-covered high-voltage electrode, together with the plastic hollow body. The intensified surface discharge is produced on the surface of the hollow body, by means of the gas nozzle with a grounded contact electrode that is manually guided over it.

Another embodiment of this device allows dry cleaning or degerming or coating of the inner surface of bottles. For this purpose, the bottle is surrounded by two halves of an electrically conductive mold, with precise fit, and high-voltage potential is applied to these halves. Together with the bottle wall, this mold acts as a dielectric-covered high-voltage electrode. In the interior of the bottle, a bottle brush made of electrically conductive material is disposed, whose bristles lie closely against the inner surface of the bottle and act as a grounded contact electrode. In this connection, the gas feed takes place by way of a holder of the bottle brush structured as a pipe. Coating of the inner wall of the bottle is achieved by mixing a suitable precursor into the process gas. If a silicon-organic compound (for example hexamethyl disiloxane HMDSO or tetraethyl orthosilicate TEOS) is used as the precursor, then $SiO_x$ layers can be produced on the surfaces both in the case of planar arrangements and in the case of inside treatment of bottles.

In another embodiment of the device, one or more dielectric-covered high-voltage electrodes are integrated into a hand-held device, in such a manner that the contact surfaces between the integrated dielectric-covered high-voltage electrodes and the grounded contact electrode are disposed in the plane of the gas exit from the gas nozzle, so that an intensified surface discharge is produced in this region, on the surface of the dielectric of the high-voltage electrode.

In other embodiments of the device, catheters and cables can be externally treated, as is explained in greater detail by the drawings relating to the exemplary embodiments. In similar arrangements, treatments and coatings of the inner surface of pipes and hoses can also be implemented according to the working principle presented here.

Advantages of the Invention

The method can be used in very flexible manner, it is suitable even for treatment of complex surface geometries, and offers the possibility of being used both in the form of a cost-advantageous hand-held device and in the form of machine-controlled systems.

Because of the low energy and gas consumption, as well as the low investment costs for the power supply devices and the treatment units, the method offers a very cost-advantageous solution for many applications.

The method permits homogeneous plasma treatment and/or plasma coating of surfaces, whereby material damage caused by electrical breakdown or thermal stress can be precluded by means of a suitable selection of the process parameters.

The method permits plasma treatment of biological tissue, whereby electrical breakdown or thermal stress can be precluded by means of a suitable selection of the process parameters.

Having generally described this invention, a further understanding can be obtained by reference to certain specific examples which are provided herein for purposes of illustration only, and are not intended to be limiting unless otherwise specified.

EXAMPLES

Figure 1:
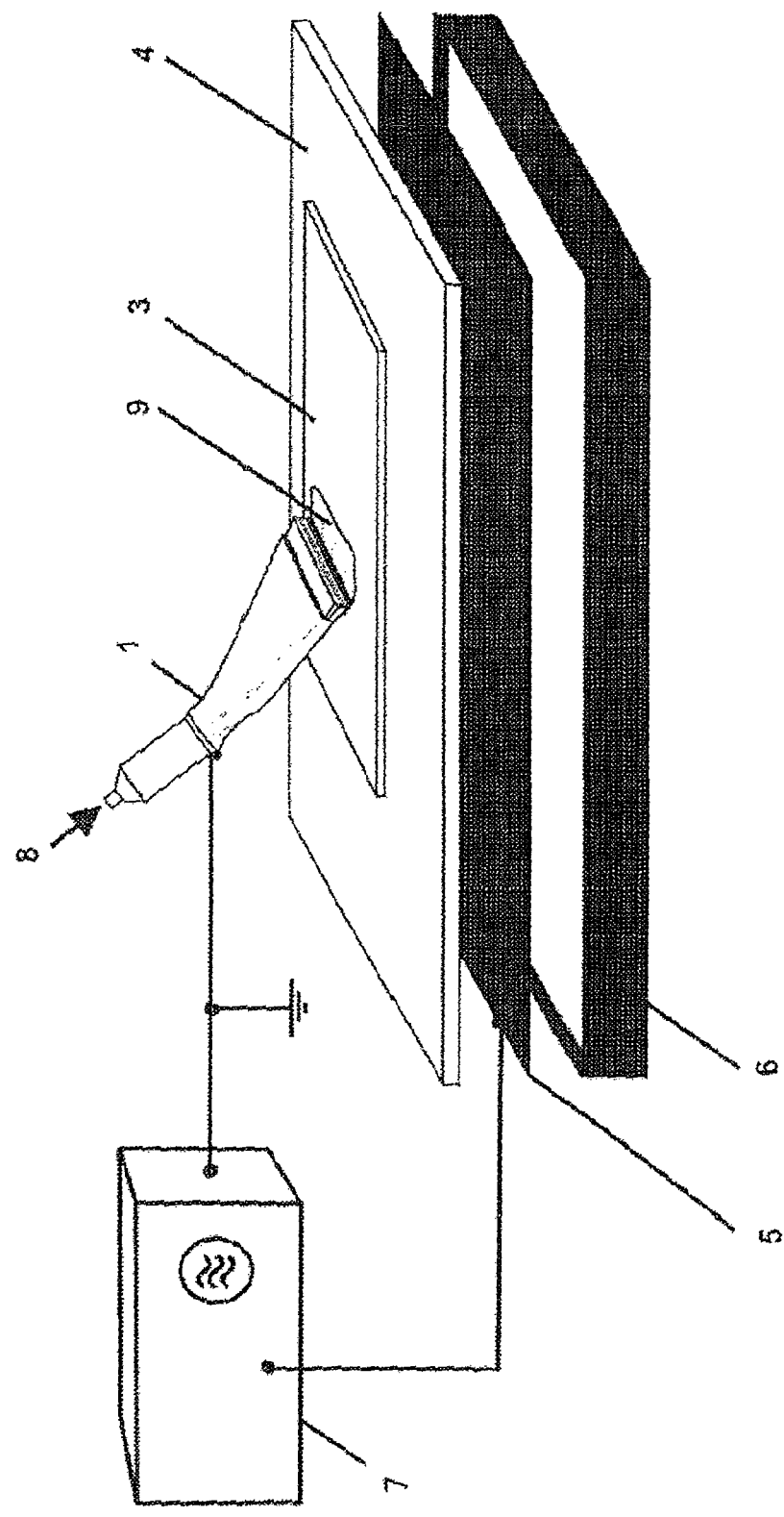
FIG. 1 shows the fundamental structure of a device having a planar high-voltage electrode (5) covered with a dielectric or ferroelectric (4), as well as having a gas nozzle (1) configured as a grounded contact electrode (2), which nozzle produces a surface plasma (9), sliding on a work piece (3) that lies on the dielectric (4). The gas feed (8) takes place by way of the gas connector of the broad jet gas nozzle (1).
Figure 2:
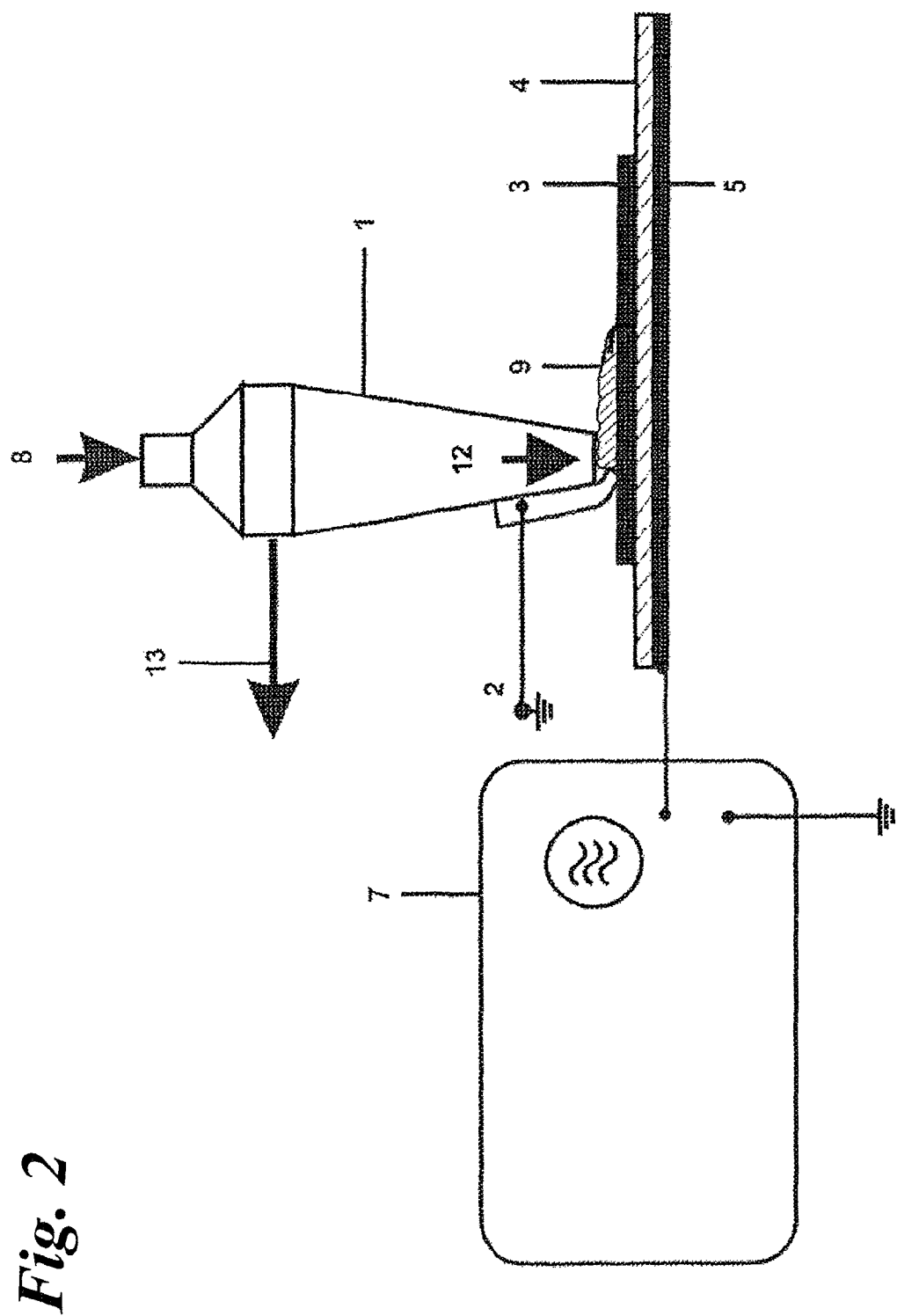
FIG. 2 shows that the grounded contact electrode (2) can be structured as a slide contact composed of electrically conductive elastomer.
Figure 3:
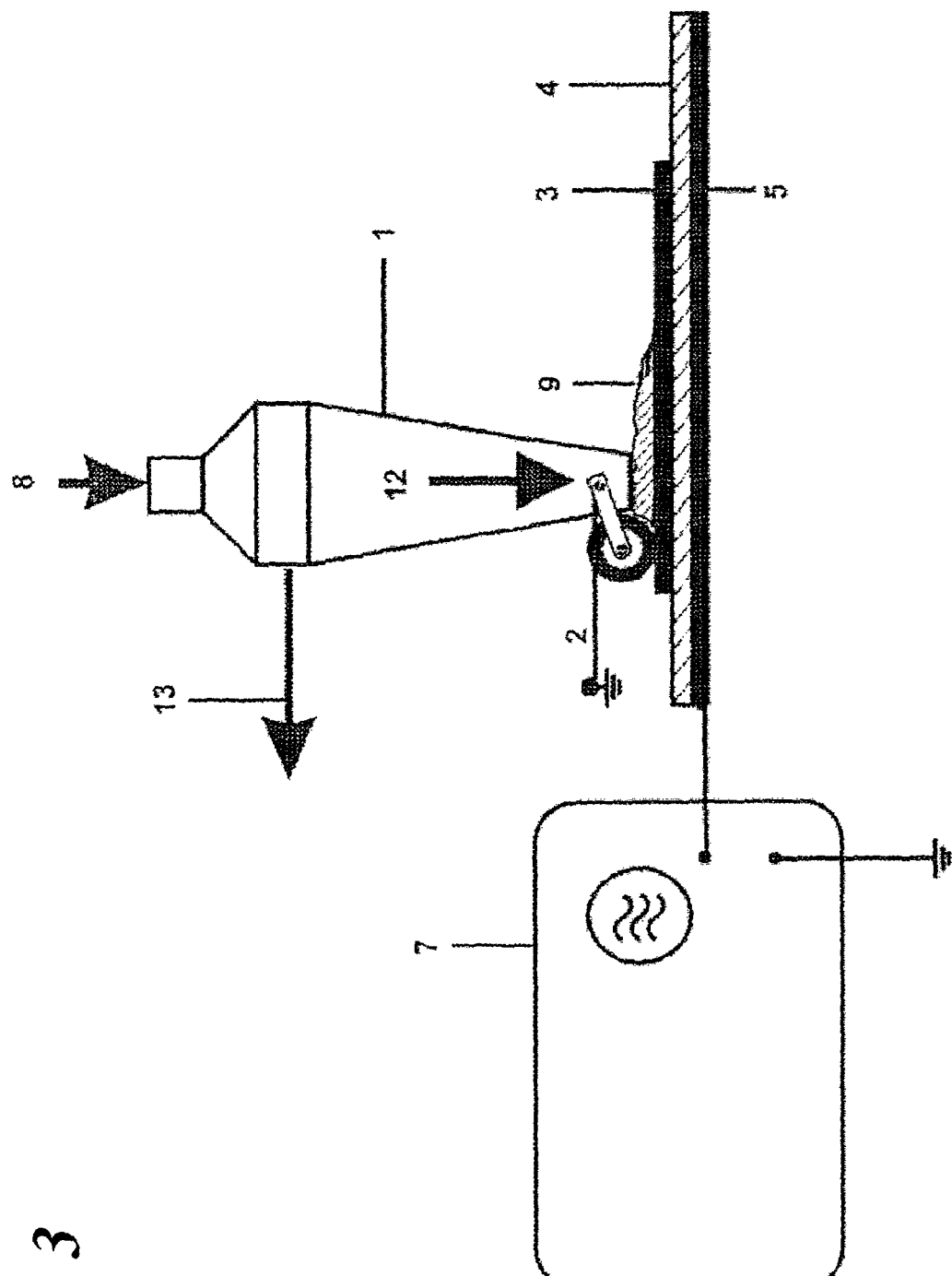
FIG. 3 shows that the grounded contact electrode (2) can be structured as an electrically conductive roller.
Figure 4:
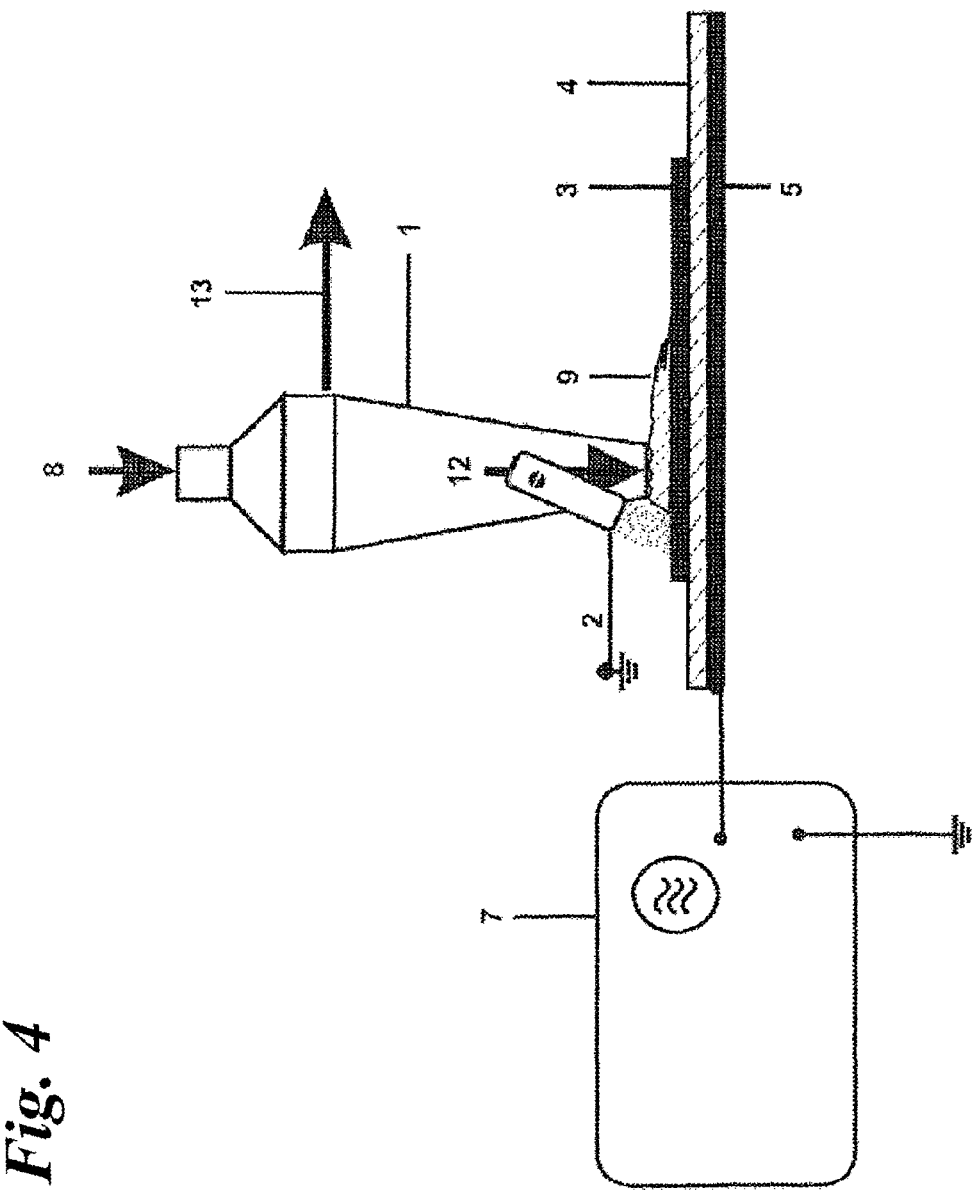
FIG. 4 shows that the grounded contact electrode (2) can be structured as a brush composed of electrically conductive bristles.
Figure 5:
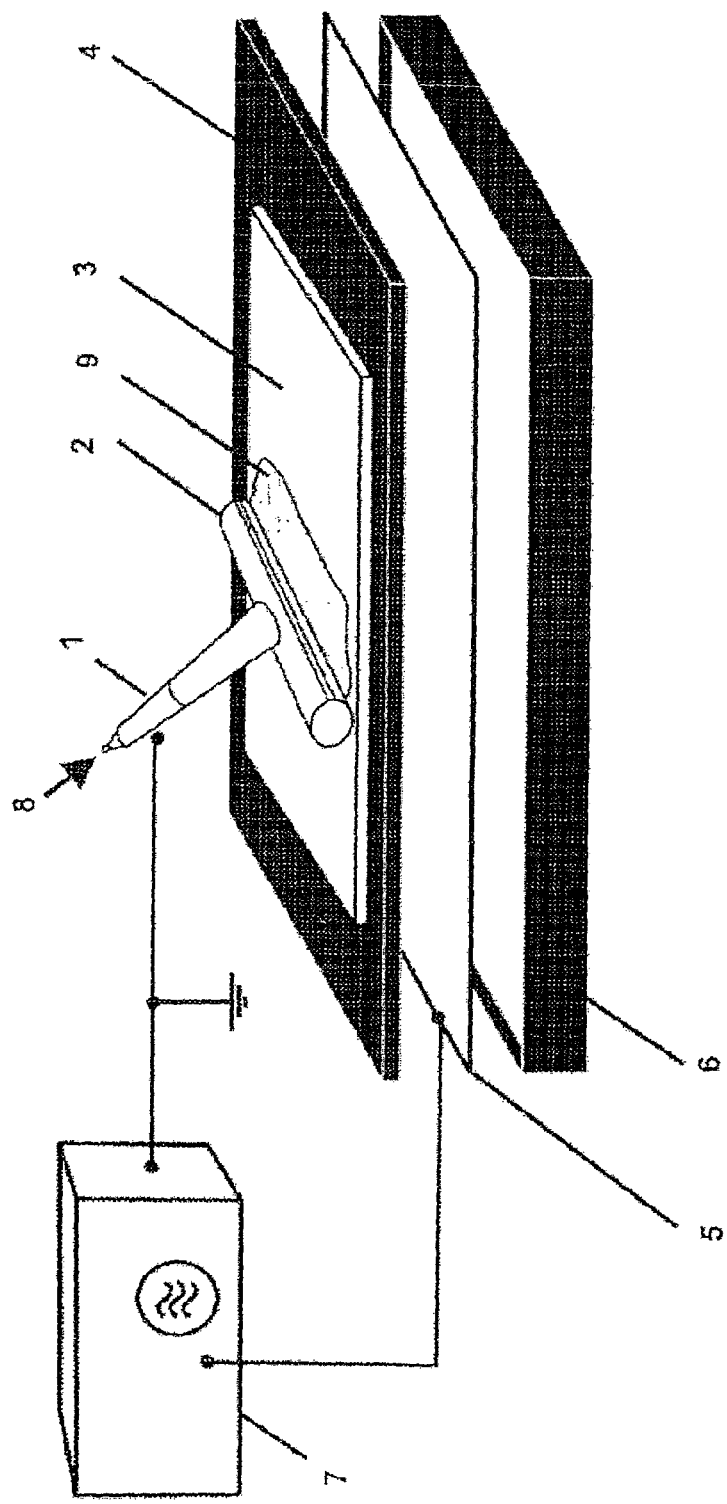
FIG. 5 shows the same structure as FIG. 1, except a metal pipe having a narrow slit for gas exit simultaneously functions as a broad jet gas nozzle (1) and as a grounded contact electrode (2).
Figure 6:
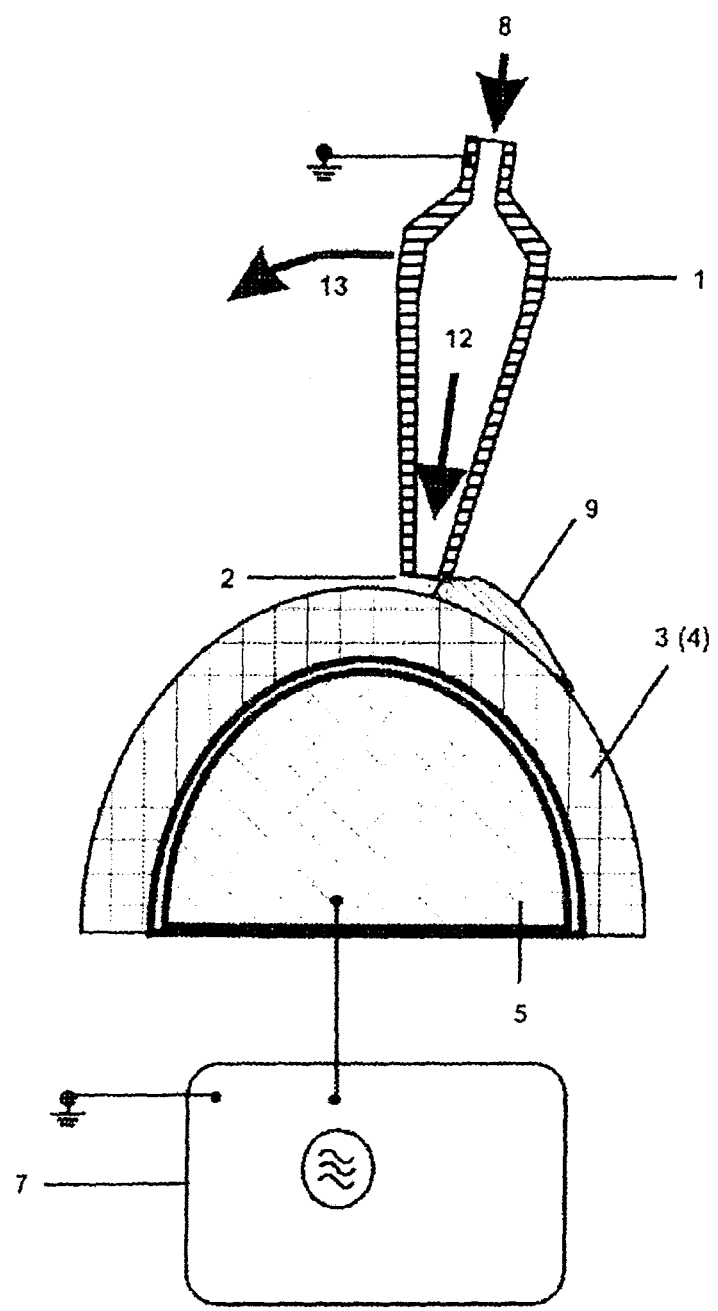
FIG. 6 shows an arrangement for treatment of hollow bodies made of plastic (3), in which an electrically conductive filling of the hollow body serves as the high-voltage electrode, and the hollow body simultaneously acts as the dielectric (4) of the high-voltage electrode.
Figure 7:
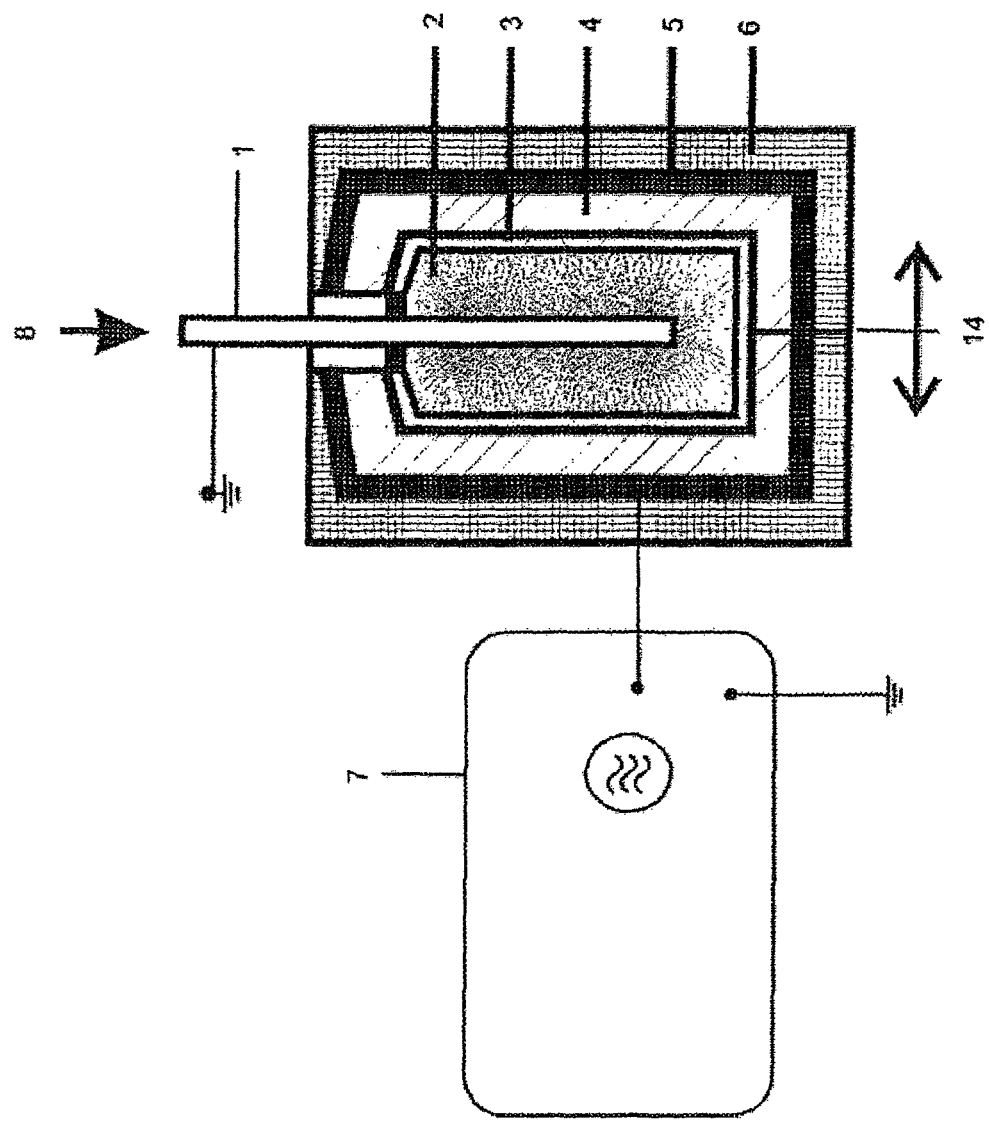
In FIG. 7, the fundamental structure for interior treatment (dry cleaning, disinfection and/or coating) of bottles is shown.
Figure 8:
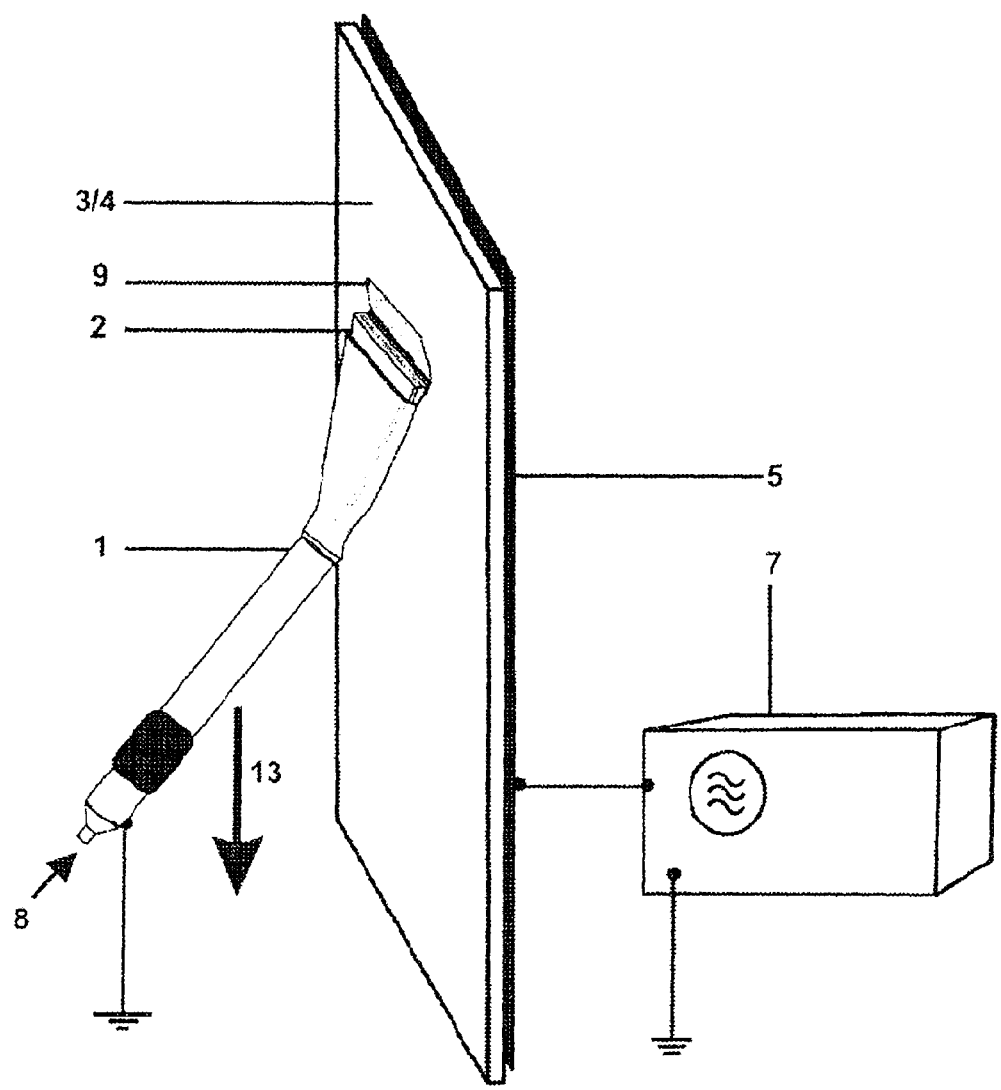
FIG. 8 shows an arrangement for dry cleaning and disinfection of specially designed tables and wall coverings in hygienically sensitive sectors, such as, for example, in operating rooms or in the sector of foods processing, as an application example. For this purpose, the coverings of the table and walls are to be configured in such a manner that they can be combined in a circuit with a high-voltage electrode (5) covered with an insulator (4).

The invention and its application possibilities are explained in greater detail with the exemplary embodiments shown below in different drawings. The following reference symbols are used to identify the individual elements of the structure of the devices:

REFERENCE SYMBOL LIST 1 gas nozzle
2 grounded contact electrode
3 work piece
4 insulator (dielectric or ferroelectric)
5 high-voltage electrode
6 insulation
7 high-voltage source
8 gas feed
9 surface plasma
10 housing with high-voltage supply
11 motor with magnetic clutch
12 gas exit
13 movement direction
14 joining edge
15 second nozzle channel
16 suction device
17 precursor feed
18 rotating brush
19 hinge
20 handle piece with plug connector FIG. 1 shows the fundamental structure of the device having a planar high-voltage electrode (5) covered with a dielectric or ferroelectric (4), as well as having a gas nozzle (1) configured as a grounded contact electrode, which nozzle produces a surface plasma (9), sliding on a work piece (3) that lies on the dielectric (4). The gas feed (8) takes place by way of the gas connector of the broad-jet gas nozzle (1). In this connection, the grounded contact electrode (2) can be structured either as a slide contact composed of electrically conductive elastomer, as shown in FIG. 2, as an electrically conductive roller, as shown in FIG. 3, or as a brush composed of electrically conductive bristles, as demonstrated in FIG. 4. FIG. 5 shows the same structure as FIG. 1, but here a metal pipe having a narrow slit for gas exit simultaneously functions as a broad-jet gas nozzle (1) and as a grounded contact electrode (2). FIG. 6 shows an arrangement for treatment of hollow bodies made of plastic (3), in which an electrically conductive filling of the hollow body serves as the high-voltage electrode, and the hollow body simultaneously acts as the dielectric (4) of the high-voltage electrode. In FIG. 7, the fundamental structure for interior treatment (dry cleaning, disinfection and/or coating) of bottles is shown. FIG. 8 shows an arrangement for dry cleaning and disinfection of specially designed tables and wall coverings in hygienically sensitive sectors, such as, for example, in operating rooms or in the sector of foods processing, as an application example. For this purpose, the coverings of the table and walls are to be configured in such a manner that they can be combined in a circuit with a high-voltage electrode (5) covered with an insulator (4). FIG. 9 demonstrates the fundamental structure of a compact hand-held device for treatment of plastic surfaces having a complex shape, in which the high-voltage electrode (5), covered with an insulator (4), is disposed in the gas nozzle (1). At the end of this high-voltage electrode, the electrically conductive, grounded contact electrode (2), structured as a screen, is disposed in the plane of the nozzle opening. The arrangement shown in FIG. 10 has a similar design. This device is intended for treatment of metal surfaces having a complex shape. Since, in this case, the metal surface itself serves as a conductive, grounded contact electrode, it is possible to do without a special contact electrode mounted on the nozzle. As shown in FIG. 12, the high-voltage electrode (5) surrounded by a dielectric (4) can also be disposed outside of the gas nozzle, in a similar device.

FIG. 11 shows another embodiment of a compact hand-held device, in which an array of multiple individual electrodes is used in place of a single insulator-covered high-voltage electrode. In this manner, surface discharges having a greater area expanse are produced, so that the required treatment times can be reduced accordingly.

Other design examples of compact hand-held devices are shown in FIG. 13 to FIG. 16. In this connection, the arrangement according to FIG. 13 is an embodiment for treatment of metal surfaces, structured as a compact multi-channel plasma nozzle, in which the metallic work piece functions as a grounded contact electrode, and that of FIG. 14 is a similar arrangement for treatment of plastic surfaces, with a metal gauze disposed in the plane of the nozzle openings as a grounded contact electrode (2). In the solutions shown in FIG. 15 and FIG. 16, the process gas flows through a perforated plate made of insulation material (6), in front of which the insulator-covered high-voltage electrode (4/5) is disposed. In this connection, FIG. 15, in a manner similar to FIG. 13, shows the case for treatment of metal surfaces (acting as a grounded contact electrode), and FIG. 16, in a manner similar to FIG. 14, shows the case of treatment of plastic surfaces (metal gauze as a grounded contact electrode). In FIG. 17, the possibility of using a compact hand-held device as shown in FIG. 9 for dry cleaning and/or disinfection of handrails (3) (for example on escalators) is demonstrated.

FIG. 18 shows two possibilities of placement of a second nozzle channel (15) for suctioning off (16) ozone that is produced by the discharge. These nozzle channels (15) can also be used, as shown in FIG. 19, for the precursor feed (17) for the coating treatment.

In FIG. 20, a motor-controlled tabletop device that functions according to the principle explained in FIG. 1 to FIG. 5 is shown. As another application example, a device for combined cleaning by means of a rotating brush (18), for dry cleaning and disinfection by means of plasma treatment by means of a device as shown in FIG. 9, and for suctioning off (16) dust and ozone by way of another nozzle (15) is shown in FIG. 21.

FIG. 22 shows the fundamental circuit schematic of the voltage supply.

In FIG. 23, a treatment unit for external treatment of insulated wires to improve their wettability, which unit is based on the working principle of the invention, is shown, and in FIG. 24, a treatment unit for dry cleaning and degerming of the outer surface of catheters, having a similar structure, is shown. In both cases, the objects to be treated act as a high-voltage electrode (5) covered with a dielectric (4), and the electrically conductive, grounded contact electrode (2) consists of two thin wires that lie closely against the objects. A pipe of insulation material consisting of two halves that are connected by hinges (19) and can be opened up allows both holding and defined positioning of the objects, as well as precisely metered gas feed (8).

FIG. 25 shows a special embodiment of the arrangement shown in FIG. 16. In this case, the gas nozzle has a flatter shape and is produced from elastic materials, as are the electrodes and the gas-permeable insulation layer in the plane of the gas exit. This arrangement permits the contact surface to lie intimately against different body surfaces, and is thus fundamentally suitable for being laid onto regions of the human body, in the manner of an elastic cuff, with close skin contact, in order to be able to treat skin areas that might be diseased with it, by means of the surface discharge that is produced.

German patent application DE 10 2007 037 406.4, filed Aug. 8, 2007 and PCT application PCT/EP2008/059840, filed Jul. 26, 2008, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A device for dry cleaning, activation, coating, modification, and/or biological decontamination of a surface using an atmospheric pressure plasma produced by a surface barrier discharge in a defined, flowing gas atmosphere, said device comprising:
   a high-voltage electrode covered by a dielectric or a ferroelectric,
   an electrically conductive grounded contact electrode,
   a high-voltage supply,
   a gas feed, and
   a gas nozzle with a gas exit opening,
   wherein
   a) the gas nozzle is integrated into the contact electrode, or
   b) the gas nozzle itself functions as a grounded contact electrode, and the gas exit opening is designed in such a manner that an exiting gas stream is directed at the contact location of the grounded contact electrode, and wherein
   c) said dielectric or ferroelectric cover of said dielectric-covered or ferroelectric-covered high-voltage electrode is in direct contact with said grounded, electrically conductive contact electrode.

2. The device according to claim 1, further comprising at least one of the following elements:
   an insulation, a housing for the high-voltage supply, a motor, with or without a magnetic clutch, joining edge, second nozzle channel, suction device, precursor feed, hinge or handle piece with plug connector.

3. The device according to claim 1, wherein a broad jet nozzle functions as the gas nozzle and the broad jet nozzle has a slit having a width of 0.2-0.3 mm.

4. The device according to claim 1, wherein a hand-held device having minimal geometric dimensions serves as the voltage source.

5. The device according to claim 1, wherein the electrically conductive, grounded contact electrode
   is structured as a slide contact or as a small roller, roll, brush, or whisk, and/or
   comprises metal or another electrically conductive material.

6. The device according to claim 1, wherein
   the surfaces to be treated are used as a dielectric-covered high-voltage electrode, and/or
   the dielectric-covered high-voltage electrode is configured as a planar mold or as a rotating roller, and/or
   the surface is surrounded by an electrically conductive mold and this mold forms the dielectric-covered high-voltage electrode.

7. The device according to claim 1, which represents a compact hand-held device in which one or more insulator-covered high-voltage electrodes are integrated into the hand-held device, together with a grounded contact electrode formed from a metal gauze or a perforated metal sheet, and are disposed in the plane of the gas exit from the gas nozzle, so that in this region, an intensified surface discharge is produced on the surface of the dielectric of the high-voltage electrodes.

8. A tabletop device for the treatment of planar materials having a restricted area expanse, comprising
   the device according to claim 1.

9. The tabletop device according to claim 8, wherein scanning of the surface, similar to an optical scanner, takes place by way of a motor drive.

10. A method for dry cleaning, activation, coating, and biological decontamination of a surface using the device according to claim 1, said method comprising:
    a) a material having said surface to be treated is situated either between the high-voltage electrode covered with a dielectric or a ferroelectric and the grounded contact electrode, or at their contact location,
    b) a process gas stream is directed out of the gas nozzle onto the contact location of the grounded contact electrode,
    c) at the same time or immediately afterward, a voltage is applied to the high-voltage electrode, and
    d) the contact electrode with the gas nozzle and the material to be treated are moved relative to one another,
    whereby a surface barrier discharge is produced in the process gas stream on the surface of the material to be treated on which the contact electrode with the gas nozzle is situated.

11. The method according to claim 10, wherein a noble gas is used in pure form or as a mixture with other gases.

12. The method according to claim 10, wherein
    the material to be treated is laid onto an insulation material layer of the planar, dielectric-covered or ferroelectric-covered high-voltage electrode, and the electrically conductive, grounded contact electrode, coupled with a broad-jet gas nozzle, is guided to slide over the plastic surface to be treated, and/or for the treatment of planar materials having a restricted area expanse, in which scanning of the surface takes place similar to an optical scanner, by way of a motor drive, and/or for advantageous treatment of longer web materials or plates, in which a dielectric-covered or ferroelectric-covered high-voltage electrode configured as a rotating roller instead of as a planar electrode is used, and the material to be treated is moved through between the rotating high-voltage electrode and the broad jet gas nozzle configured as the grounded contact electrode, which slides or rolls on the surface of the material, by means of a suitable advancing device.

13. The method according to claim 10, wherein hollow bodies made of plastic are treated, in that the hollow bodies are filled with a conductive mass, which mass is connected with the high voltage and thus acts as a dielectric-covered high-voltage electrode, together with the hollow plastic body, or for dry cleaning and/or biological decontamination of the inner surface of bottles, the bottle is surrounded by two halves of an electrically conductive mold, with precise fit, to which halves high-voltage potential is applied, which mold, together with the bottle wall, acts as a dielectric-covered high-voltage electrode, and in the interior of the bottle, a bottle brush made of electrically conductive material is disposed, having bristles that lie closely against the inner surface of the bottle, which acts as a grounded contact electrode, at the same time, and is coupled with a gas nozzle.

14. The method according to claim 10, wherein for external treatment of insulated wires, in order to improve their wettability, the wires to be treated are used as a dielectric-covered high-voltage electrode and are disposed in a pipe made of insulation material, together with the electrically conductive, grounded contact electrodes, consisting of two thin wires, which lie closely against the wire to be treated.

15. The method according to claim 10, wherein a precursor is added to the process gas, directly or by way of a second nozzle, in order to produce $SiO_x$ layers, for coating of inner and outer surfaces.

16. The method according to claim 15, wherein said precursor is a silicon-organic compound.

17. The method according to claim 10, wherein a continuous or pulsed alternating voltage, pulsed direct voltage, or individual high-voltage pulses are used as the high-voltage supply.

18. The device according to claim 1, which is suitable for
a) treatment of surfaces in operating rooms, or
b) treatment of surfaces in the foods sector, or
c) treatment of metal surfaces, or
d) treatment of plastic surfaces, or
e) cleaning and disinfection of stair handrails, or
f) removal of parting agent residues from surfaces, or
g) external treatment of insulated wires, or
h) dry cleaning, disinfection, and biological decontamination of hoses used in medical devices or instruments, or
i) treatment or coating of the inner surfaces of pipes or hoses, or
j) healing of skin diseases, or
k) treatment of biological tissue, particularly wounds, or
l) plasma treatment of films or signs made of plastic.

19. The method according to claim 10, which is suitable for
a) treatment of surfaces in operating rooms, or
b) treatment of surfaces in the foods sector, or
c) treatment of metal surfaces, or
d) treatment of plastic surfaces, or
e) cleaning and disinfection of stair handrails, or
f) removal of parting agent residues from surfaces, or
g) external treatment of insulated wires, or
h) dry cleaning, disinfection, and biological decontamination of hoses used in medical devices or instruments, or
i) treatment or coating of the inner surfaces of pipes or hoses, or
j) healing of skin diseases, or
k) treatment of biological tissue, particularly wounds, or
l) plasma treatment of films or signs made of plastic.

20. The method according to claim 13, wherein said conductive mass is steel wool, a conductive plastic material or an electrically conductive fluid.

21. The device according to claim 18, which is suitable for plasma treatment of films or signs made of plastic to improve the adhesion of adhesive films or printing inks on these materials.

22. The method according to claim 19, which is suitable for plasma treatment of films or signs made of plastic to improve the adhesion of adhesive films or printing inks on these materials.

* * * * *